United States Patent
Hu et al.

(10) Patent No.: US 9,421,133 B2
(45) Date of Patent: *Aug. 23, 2016

(54) CLOSED INCISION NEGATIVE PRESSURE WOUND THERAPY DEVICE AND METHODS OF USE

(71) Applicant: KCI Licensing, Inc., San Antonio, TX (US)

(72) Inventors: Dean Hu, Sunnyvale, CA (US); Moshe Pinto, Sunnyvale, CA (US); Kenton Fong, Sunnyvale, CA (US); Akshay Mavani, Sunnyvale, CA (US); Kenneth Wu, Sunnyvale, CA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/484,578

(22) Filed: Sep. 12, 2014

(65) Prior Publication Data

US 2015/0005722 A1    Jan. 1, 2015

Related U.S. Application Data

(63) Continuation of application No. 14/058,175, filed on Oct. 18, 2013, now Pat. No. 8,834,434, which is a continuation of application No. 13/004,819, filed on Jan. 11, 2011, now Pat. No. 8,562,576, which is a continuation of application No. 12/249,759, filed on Oct. 10, 2008, now Pat. No. 8,246,590.

(60) Provisional application No. 60/979,315, filed on Oct. 11, 2007.

(51) Int. Cl.
*A61M 5/00* (2006.01)
*A61M 35/00* (2006.01)
(Continued)

(52) U.S. Cl.
CPC ..... *A61F 13/0226* (2013.01); *A61F 13/00063* (2013.01); *A61F 13/02* (2013.01);
(Continued)

(58) Field of Classification Search
CPC ........ A61M 5/00; A61M 5/32; A61M 25/00; A61M 35/00; A61M 1/00; A61M 5/178; A61F 13/00; A61F 7/00
See application file for complete search history.

(56) References Cited

U.S. PATENT DOCUMENTS

| 114,750 A | 5/1871 | Battersby et al. |
| 2,012,755 A | 8/1935 | De Muth |

(Continued)

FOREIGN PATENT DOCUMENTS

| CN | 2851641 Y | 12/2006 |
| DE | 202005019670 U1 | 4/2006 |

(Continued)

OTHER PUBLICATIONS

US 7,186,244, 3/2007, Hunt et al. (withdrawn).

(Continued)

*Primary Examiner* — Adam Marcetich
*Assistant Examiner* — Ilya Treyger

(57) ABSTRACT

A surgical tissue therapy device includes a sealant layer and a collection chamber. The sealant layer functions so as to create a sealed enclosure or space between it and the surface of a patient by forming, preferably, an airtight seal around a surgical area of skin trauma. The closed incision tissue therapy device also comprises a collection chamber, which may comprise an elongate tubular chamber with a plurality of longitudinally spaced openings. The collection chamber may be configured to be in fluid communication with the sealant layer and the area of skin trauma and functions as to distribute the negative pressure applied to a surgically closed area of skin trauma. Preferably, the pressure under the sealant layer is reduced by expanding the volume of the enclosure space and thereby decreasing the density of air molecules under the sealant layer. The collection material may comprise a material and/or a configuration that permits length changes based upon the length of the corresponding surgical wound or incision.

19 Claims, 14 Drawing Sheets

(51) Int. Cl.
*A61F 13/00* (2006.01)
*A61F 13/02* (2006.01)
*A61M 1/00* (2006.01)
*A61M 27/00* (2006.01)
*A61M 5/32* (2006.01)
*A61M 25/00* (2006.01)

(52) U.S. Cl.
CPC ....... *A61F13/0216* (2013.01); *A61F 13/0266* (2013.01); *A61M 1/0088* (2013.01); *A61M 27/00* (2013.01); *A61M 35/00* (2013.01); *A61F 13/00068* (2013.01); *A61F 2013/00174* (2013.01); *A61F 2013/00536* (2013.01)

(56) References Cited

U.S. PATENT DOCUMENTS

| | | |
|---|---|---|
| 2,198,666 A | 4/1940 | Benjamin |
| 2,472,116 A | 6/1949 | Maynes |
| 2,531,757 A | 11/1950 | Whinery |
| 2,660,342 A | 11/1953 | Herman |
| 2,863,452 A | 12/1958 | Edna |
| 3,334,628 A | 8/1967 | Saemann et al. |
| 3,487,836 A | 1/1970 | Niebel et al. |
| 3,528,426 A | 9/1970 | Vukojevic et al. |
| 3,583,399 A | 6/1971 | Ritsky |
| 3,628,325 A | 12/1971 | Morita |
| 3,680,560 A | 8/1972 | Pannier, Jr. et al. |
| 3,779,243 A | 12/1973 | Tussey et al. |
| 3,809,086 A | 5/1974 | Schachet et al. |
| 3,809,087 A | 5/1974 | Lewis, Jr. |
| 3,833,030 A | 9/1974 | Waldbauer, Jr. et al. |
| 3,841,331 A | 10/1974 | Wilder et al. |
| 3,982,546 A | 9/1976 | Friend |
| 4,041,934 A | 8/1977 | Genese |
| 4,080,970 A | 3/1978 | Miller |
| 4,278,089 A | 7/1981 | Huck et al. |
| 4,333,456 A | 6/1982 | Webb |
| 4,333,458 A | 6/1982 | Margulies et al. |
| D265,423 S | 7/1982 | Abraham et al. |
| 4,382,441 A | 5/1983 | Svedman |
| 4,404,924 A | 9/1983 | Goldberg et al. |
| 4,525,167 A | 6/1985 | Goldberg et al. |
| 4,535,772 A | 8/1985 | Sheehan |
| 4,549,554 A | 10/1985 | Markham |
| 4,578,060 A | 3/1986 | Huck et al. |
| 4,648,870 A | 3/1987 | Goldberg et al. |
| 4,664,128 A | 5/1987 | Lee |
| 4,743,232 A | 5/1988 | Kruger |
| 4,758,232 A | 7/1988 | Chak |
| 4,867,748 A | 9/1989 | Samuelsen |
| 4,882,337 A | 11/1989 | Cussans |
| 4,929,577 A | 5/1990 | Cornell |
| 4,969,880 A | 11/1990 | Zamierowski |
| 5,071,409 A | 12/1991 | Rosenberg |
| 5,100,396 A | 3/1992 | Zamierowski |
| 5,116,310 A | 5/1992 | Seder et al. |
| 5,116,610 A | 5/1992 | Broaddus |
| 5,157,808 A | 10/1992 | Sterner, Jr. |
| 5,195,977 A | 3/1993 | Pollitt |
| 5,234,462 A | 8/1993 | Pavletic |
| 5,261,893 A | 11/1993 | Zamierowski |
| 5,263,922 A | 11/1993 | Sova et al. |
| 5,266,476 A | 11/1993 | Sussman et al. |
| 5,395,345 A | 3/1995 | Gross |
| 5,527,293 A | 6/1996 | Zamierowski |
| 5,549,584 A | 8/1996 | Gross |
| 5,636,643 A | 6/1997 | Argenta et al. |
| 5,645,081 A | 7/1997 | Argenta et al. |
| 5,662,714 A | 9/1997 | Charvin et al. |
| 5,701,917 A | 12/1997 | Khouri |
| 5,704,905 A | 1/1998 | Jensen et al. |
| 5,711,969 A | 1/1998 | Patel et al. |
| 6,071,267 A | 6/2000 | Zamierowski |
| 6,135,116 A | 10/2000 | Vogel et al. |
| 6,142,982 A | 11/2000 | Hunt et al. |
| 6,235,964 B1 | 5/2001 | Kadash et al. |
| 6,333,093 B1 | 12/2001 | Burrell et al. |
| 6,345,623 B1 | 2/2002 | Heaton et al. |
| 6,458,109 B1 | 10/2002 | Henley et al. |
| 6,461,467 B2 | 10/2002 | Blatchford et al. |
| 6,468,237 B1 | 10/2002 | Lina |
| 6,520,982 B1 | 2/2003 | Boynton et al. |
| 6,553,998 B2 | 4/2003 | Heaton et al. |
| 6,557,704 B1 | 5/2003 | Randolph |
| 6,685,681 B2 | 2/2004 | Lockwood et al. |
| 6,695,823 B1 | 2/2004 | Lina et al. |
| 6,695,824 B2 | 2/2004 | Howard et al. |
| 6,712,839 B1 | 3/2004 | Lonne |
| 6,752,794 B2 | 6/2004 | Lockwood et al. |
| 6,755,807 B2 | 6/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,825,246 B1 | 11/2004 | Fattman |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,986,234 B2 | 1/2006 | Liedtke |
| 6,994,702 B1 | 2/2006 | Johnson |
| 7,004,915 B2 | 2/2006 | Boynton et al. |
| 7,066,182 B1 | 6/2006 | Dunshee |
| 7,070,584 B2 | 7/2006 | Johnson et al. |
| 7,077,832 B2 | 7/2006 | Fleischmann |
| 7,117,869 B2 | 10/2006 | Heaton et al. |
| 7,144,390 B1 | 12/2006 | Hannigan et al. |
| 7,198,046 B1 | 4/2007 | Argenta et al. |
| 7,216,651 B2 | 5/2007 | Argenta et al. |
| 7,273,054 B2 | 9/2007 | Heaton et al. |
| 7,279,612 B1 | 10/2007 | Heaton et al. |
| 7,316,672 B1 | 1/2008 | Hunt et al. |
| 7,351,250 B2 | 4/2008 | Zamierowski |
| 7,361,185 B2 | 4/2008 | O'Malley et al. |
| 7,381,211 B2 | 6/2008 | Zamierowski |
| 7,381,859 B2 | 6/2008 | Hunt et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,429,265 B2 | 9/2008 | O'Malley et al. |
| 7,461,158 B2 | 12/2008 | Rider et al. |
| 7,485,112 B2 | 2/2009 | Karpowicz et al. |
| 7,520,872 B2 | 4/2009 | Biggie et al. |
| 7,534,240 B1 | 5/2009 | Johnson |
| 7,553,306 B1 | 6/2009 | Hunt et al. |
| 7,611,500 B1 | 11/2009 | Lina et al. |
| 7,645,269 B2 | 1/2010 | Zamierowski |
| 7,662,112 B2 | 2/2010 | Zamierowski et al. |
| 7,678,102 B1 | 3/2010 | Heaton |
| 7,683,234 B2 | 3/2010 | Gurtner et al. |
| 7,700,819 B2 | 4/2010 | Ambrosio et al. |
| 8,083,712 B2 | 12/2011 | Biggie et al. |
| 8,435,221 B2 | 5/2013 | Hu et al. |
| 8,562,576 B2 | 10/2013 | Hu et al. |
| 8,834,434 B2 | 9/2014 | Hu et al. |
| 2001/0025166 A1 | 9/2001 | Campbell |
| 2001/0031943 A1 | 10/2001 | Urie |
| 2001/0043943 A1 | 11/2001 | Coffey |
| 2002/0150720 A1 | 10/2002 | Howard et al. |
| 2002/0173808 A1 | 11/2002 | Houser et al. |
| 2002/0183702 A1 | 12/2002 | Henley et al. |
| 2003/0050594 A1 | 3/2003 | Zamierowski |
| 2004/0193187 A1 | 9/2004 | Boehringer et al. |
| 2004/0249353 A1 | 12/2004 | Risks et al. |
| 2005/0070835 A1 | 3/2005 | Joshi |
| 2005/0101940 A1 | 5/2005 | Radl et al. |
| 2005/0131327 A1 | 6/2005 | Lockwood et al. |
| 2005/0148921 A1 | 7/2005 | Hsu |
| 2005/0209574 A1 | 9/2005 | Boehringer et al. |
| 2005/0261642 A1 | 11/2005 | Weston |
| 2006/0064125 A1 | 3/2006 | Henderson et al. |
| 2006/0079852 A1 | 4/2006 | Bubb et al. |
| 2006/0282028 A1 | 12/2006 | Howard et al. |

(56) References Cited

U.S. PATENT DOCUMENTS

| | | |
|---|---|---|
| 2007/0027414 A1 | 2/2007 | Hoffman et al. |
| 2007/0032755 A1 | 2/2007 | Walsh |
| 2007/0185426 A1 | 8/2007 | Ambrosio et al. |
| 2007/0219512 A1 | 9/2007 | Heaton et al. |
| 2007/0219532 A1 | 9/2007 | Karpowicz et al. |
| 2007/0225663 A1 | 9/2007 | Watt et al. |
| 2008/0004559 A1 | 1/2008 | Riesinger |
| 2008/0033334 A1 | 2/2008 | Gurtner et al. |
| 2008/0063615 A1 | 3/2008 | MacDonald et al. |
| 2008/0082059 A1 | 4/2008 | Fink et al. |
| 2008/0108977 A1 | 5/2008 | Heaton et al. |
| 2008/0132820 A1 | 6/2008 | Buckman et al. |
| 2008/0147115 A1 | 6/2008 | O'Malley et al. |
| 2008/0200906 A1 | 8/2008 | Sanders et al. |
| 2008/0306448 A1 | 12/2008 | Lee |
| 2008/0306456 A1 | 12/2008 | Riesinger |
| 2008/0312685 A1 | 12/2008 | O'Malley et al. |
| 2009/0012482 A1 | 1/2009 | Pinto et al. |
| 2009/0076467 A1 | 3/2009 | Pinto et al. |
| 2009/0105670 A1 | 4/2009 | Bentley et al. |
| 2009/0131845 A1 | 5/2009 | Gurtner et al. |
| 2009/0131846 A1 | 5/2009 | Gurtner et al. |
| 2009/0163844 A1 | 6/2009 | Gurtner et al. |
| 2009/0259203 A1 | 10/2009 | Hu et al. |
| 2009/0293887 A1 | 12/2009 | Wilkes et al. |
| 2009/0299249 A1 | 12/2009 | Wilkes et al. |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299303 A1 | 12/2009 | Seegert |
| 2009/0299307 A1 | 12/2009 | Barta et al. |
| 2009/0299308 A1 | 12/2009 | Kazala, Jr. et al. |
| 2009/0299340 A1 | 12/2009 | Kazala, Jr. et al. |
| 2009/0299341 A1 | 12/2009 | Kazala, Jr. et al. |
| 2009/0299342 A1 | 12/2009 | Cavanaugh, II et al. |
| 2009/0312728 A1 | 12/2009 | Randolph et al. |
| 2010/0042021 A1 | 2/2010 | Hu et al. |
| 2010/0087767 A1 | 4/2010 | McNeil |
| 2010/0106117 A1 | 4/2010 | Lockwood et al. |
| 2010/0137775 A1 | 6/2010 | Hu |
| 2010/0137817 A1 | 6/2010 | Hardman et al. |
| 2010/0210986 A1 | 8/2010 | Sanders et al. |
| 2011/0130691 A1 | 6/2011 | Hu |
| 2011/0137270 A1 | 6/2011 | Hu et al. |
| 2011/0313377 A1 | 12/2011 | Pinto et al. |
| 2012/0029487 A1 | 2/2012 | Wilkes et al. |
| 2012/0046586 A1 | 2/2012 | Gurtner et al. |
| 2012/0046591 A1 | 2/2012 | Gurtner et al. |
| 2012/0078207 A1 | 3/2012 | Hu et al. |
| 2013/0006204 A1 | 1/2013 | Hu |
| 2013/0172857 A1 | 7/2013 | Hu et al. |
| 2013/0178897 A1 | 7/2013 | Wu et al. |
| 2014/0243767 A1 | 8/2014 | Hu et al. |
| 2015/0025486 A1 | 1/2015 | Hu et al. |

FOREIGN PATENT DOCUMENTS

| | | |
|---|---|---|
| GB | 2195255 A | 4/1988 |
| GB | 2306107 A | 4/1997 |
| GB | 2423019 A | 8/2006 |
| GB | 2431351 A | 4/2007 |
| JP | 2002507142 | 3/2002 |
| JP | 2005532134 A | 10/2005 |
| JP | 2007531567 A | 11/2007 |
| WO | WO-80/02182 A1 | 10/1980 |
| WO | WO-94/20041 A1 | 9/1994 |
| WO | WO-99/01173 A1 | 1/1999 |
| WO | WO-01/085035 A2 | 11/2001 |
| WO | WO-2004/006782 A1 | 1/2004 |
| WO | WO-2006/031698 A2 | 3/2006 |
| WO | WO-2006/124671 A2 | 11/2006 |
| WO | WO-2007/041642 A2 | 4/2007 |
| WO | WO-2007/092397 A2 | 8/2007 |
| WO | WO-2008/019051 A2 | 2/2008 |
| WO | WO-2008/048527 A2 | 4/2008 |
| WO | WO-2008064502 A1 | 6/2008 |
| WO | WO-2008/100437 A1 | 8/2008 |
| WO | WO-2008/112304 A1 | 9/2008 |
| WO | WO-2008136998 A1 | 11/2008 |
| WO | WO-2009/049232 A1 | 4/2009 |
| WO | WO-2009/103031 A1 | 8/2009 |
| WO | WO-2009/112848 A1 | 9/2009 |
| WO | WO-2009/146441 A1 | 12/2009 |
| WO | WO-2009/158123 A2 | 12/2009 |
| WO | WO-2009/158124 A1 | 12/2009 |
| WO | WO-2009/158125 A1 | 12/2009 |
| WO | WO-2009/158126 A1 | 12/2009 |
| WO | WO-2009/158127 A1 | 12/2009 |
| WO | WO-2009/158128 A2 | 12/2009 |
| WO | WO-2009/158129 A1 | 12/2009 |
| WO | WO-2009/158130 A1 | 12/2009 |
| WO | WO-2009/158131 A1 | 12/2009 |
| WO | WO-2009/158132 A1 | 12/2009 |
| WO | WO-2009/158133 A2 | 12/2009 |
| WO | WO 2015/123340 | 8/2015 |

OTHER PUBLICATIONS

U.S. Appl. No. 11/914,189, filed Nov. 12, 2007, Archibald et al.

"Profile". The American Heritage Dictionary of the English Language, Fourth Edition, 2000.

International Search Report mailed Dec. 11, 2008, for PCT Application No. PCT/US08/79613, filed Oct. 10, 2008, two pages.

Prevena Product Launch Video http://www.kci1.com/KCI1/prevena.

Previna Product Launch Video http://es.kci3.com/UK-ENG/prevena.

Written Opinion mailed Dec. 11, 2008, for PCT Application No. PCT/US/08/79613, filed Oct. 10, 2008, eight pages.

CLOSED INCISION NEGATIVE PRESSURE WOUND THERAPY DEVICE AND METHODS OF USE

CROSS-REFERENCE TO RELATED APPLICATIONS

The present application is a continuation and claims priority under 35 U.S.C. §120 of co-pending U.S. patent application Ser. No. 14/058,175, filed on Oct. 18, 2013, titled "CLOSED INCISION NEGATIVE PRESSURE WOUND THERAPY DEVICE AND METHODS OF USE," which is a continuation of U.S. patent application Ser. No. 13/004,819, filed on Jan. 11, 2011, which is a continuation of U.S. patent application Ser. No. 12/249,759, filed on Oct. 10, 2008, which claims priority under 35 U.S.C. §119(e) to U.S. Provisional Application Ser. No. 60/979,315 filed on Oct. 11, 2007. Priority of the aforementioned filing dates is hereby claimed and the disclosures of the patent applications are hereby incorporated by reference in their entirety.

BACKGROUND

There are millions of closed incisions (surgical or non surgical) each year, that occur in settings ranging from office-based procedures and ambulatory surgical centers to traditional in-patient hospital settings. Post-procedural care of these incisions may vary, but can involve simple use of gauze, wraps and tapes. In addition, irrigation of the wound prior to closure and meticulous sterile technique has also been advocated. Wound infections following invasive procedures and surgeries presents a potential risk to patients that can be as high as 10% with abdominal surgeries, for example. Wound infections are a significant morbidity for patients, clinicians, and hospitals and can be costly to taxpayers and other payors. Patients with wound infections may need IV antibiotics, prolonged hospitalization, wound opening and dressing changes, and some go on to develop wound dehiscence and enterocutaneous fistulas. While preoperative prophylactic antibiotics have been shown to decrease post-operative wound infection, post-operative antibiotics have not.

SUMMARY

Provided herein is a device for treating a surgically closed incision. In one embodiment of the device provided herein, the device comprises a sealant layer and a collection chamber. In some embodiments, the sealant layer may be adapted and configured to create a seal around a surgically closed area of skin trauma, thereby forming a sealed enclosure or space. In addition, the collection chamber may be adapted and configured to distribute pressure changes throughout at least a portion of the sealed enclosure or space created by the sealant layer.

Further provided herein is a device for the treatment of a closed incision wherein the device further comprises a suction source. The suction source may be in fluid communication with the sealed enclosure. In some embodiments of the device, the suction source may be adapted and configured to reduce the level of pressure located inside of the sealed enclosure. In some embodiments, the device may comprise a contact layer. The contact layer may be adapted and configured to be in communication with the collection chamber of the device. In some embodiments, the contact layer has a conduit or opening that permits fluid communication with the collection chamber.

In a further embodiment of the device, the device may comprise a protective layer. The protective layer may be used to affix the contact layer to the surgically closed area of skin trauma. In an embodiment where a protective layer is used, the protective layer may be further adapted and configured to protect the skin adjacent to the surgically closed area of skin trauma.

Also provided herein is a closed incision therapy device, comprising a collection chamber. In some embodiments, the collection chamber may be in a pre-evacuated state before the collection chamber is used with the device. In some embodiments, the collection chamber is deformable or bendable by the user or healthcare provider. In a further embodiment, the collection chamber comprises a flexible tube. The flexible tube may be configured to deform or bend in response to changes in the surface topology of the surgically closed area of skin trauma.

In a further embodiment of the device described herein, the collection chamber comprises a flexible tube with discrete collection members for collecting exudate or other suitable material. In some embodiments, the flexible tube comprises a single discrete collection member, but in other embodiments, the flexible tube comprises two or more discrete collection members. At least one of the discrete collection chambers may be in communication with the flexible tubing. For example, the discrete collection members may be in fluid communication with the flexible tubing. In an embodiment where at least two discrete collection members are used, the discrete collection members may be in communication with other discrete collection members and may be separated by a segment of flexible tubing. In some embodiments, two or more of the discrete collection members may be in fluid communication with each other. In some embodiments, the flexible tubing and the discrete collection members are adapted and configured to be integrated with the sealant layer, while in other embodiments, the discrete collection members but not the flexible tubing are adapted and configured to be integrated with the sealant layer. In a further embodiment of the collection chamber provided herein, the collection chamber may comprise a series of openings. In such an embodiment, the series of openings are adapted and configured to provide fluid communication between the collection chamber and the surgically closed area of skin trauma.

In some embodiments, the collection chamber comprises a support integrated into the walls of the collection chamber. The support structure may be adapted and configured to allow the user to shape the collection chamber into a particular configuration. The support structure may further maintain or resist changes to the shape of the particular configuration, or at least until a new configuration is desired by the user.

In some embodiments, the collection chamber preferably comprises a one-way flow valve. In some embodiments, the one way flow valve is adapted and configured to facilitate the emptying of the collection chamber. The one-way flow valve may be further adapted and configured to facilitate the re-creation of a reduced level of pressure inside the collection chamber and/or to restore the collection chamber to its original pre-evacuated state.

In some embodiments, the collection chamber may be a dual chamber collection chamber. For example, the dual chamber collection chamber may comprise a first chamber and a second chamber, where the first and second chamber are in communication with each other. In some embodiments, the second chamber may further comprise an actuating and/or regulating mechanism. The actuating and/or regulating mechanism may be a non-powered or passive actuating mechanism. In such an embodiment, the second chamber is adapted and configured to expand a volume of air located in a joint volume of space shared between the sealed enclosure and the dual chamber collection chamber. In some embodiments, the dual chamber collection chamber comprises a reciprocating mechanism.

As mentioned above, the device may further comprise a contact layer. The contact layer may serve as a vehicle for the delivery of one or more agents that augment the healing process. In some embodiments, the agents may include a pharmacological or biological agent. In some embodiments, the contact layer is a porous dressing interface.

In some embodiments, a wound treatment device may be adapted and configured to conform to the length of the surgically closed area of skin trauma. In other embodiments, the wound treatment device may be cut to size. In some examples, the collection chamber of the wound treatment device is adapted and configured to conform to the length of the surgically closed area of skin trauma. In other examples, the contact layer and/or the sealant layer may be configured to conform to the length of the surgically closed area of skin trauma. In some embodiments, the sealant layer may be configured to be semi-rigid. In such an embodiment, the sealant layer may be configured to provide tensile support to the surgically closed area of skin trauma. In such an embodiment, the sealant layer may be adapted to alleviate mechanical tension.

In some embodiments, the device may further comprise absorbent beads or other absorbent structures. In some embodiments the device may further comprise antimicrobial agents. In some embodiments, the device is configured to be emptied and further configured to be re-evacuated. In some embodiments, the device is configured to deliver reduced pressure between about 0.001 to about 1 atmosphere. In some embodiments the level of atmospheric pressure underneath the sealant layer may be reduced to about 0.001 atm or higher, but in other embodiments to about 0.005 atm, about 0.01 atm, about 0.05 atm, about 0.1 atm, about 0.2 atm, about 0.5 atm, about 0.7 atm, or about 0.9 atm. In some embodiments, the atmospheric pressure underneath the sealant layer is reduced to less than about 0.8 atm, about 0.7 atm, about 0.6 atm, about 0.4 atm, about 0.3 atm, about 0.2 atm, about 0.1 atm, about 0.07 atm, about 0.03 atm, about 0.007 atm, or even to less than about 0.003 atm.

In some embodiments of the device provided herein, the contact layer, the sealant layer, and/or the collection chamber are further configured to be translucent or transparent so as to facilitate application to the incision site.

In another embodiment, a wound treatment device is provided, wherein the wound treatment device comprises a flexible sealant structure with an upper surface, a lower surface and an adhesive, a collection structure integrally formed with the flexible sealant structure and comprising a wall and an internal space surrounded by the wall, and a plurality of passageways between the internal space of the collection structure and the lower surface of the flexible sealant structure and passing through the wall of the collection structure and through the upper surface of the flexible sealant structure. In some examples, there are at least three passageways. Also, in some examples the device further comprises a suction source and/or a suction port in fluid communication with the internal space of the collection structure. The suction source may comprise a constant force spring and/or a sliding seal. In some instances, the suction source has a fixed external profile independent of its internal pressure level. In some specific examples, the suction source may be integrally formed with the collection structure. In regards to the collection structures, the collection structure may be a collection tube comprising a first end and a second end, and the plurality of passageways may be longitudinally spaced between the first and the second end of the collection tube. In some instances, the collection structure may be a flexible collection structure.

In another embodiment, a method for treating a closed incision is provided, where the method or procedure comprises forming a sealed space along a closed incision using a sealant layer, wherein the closed incision was formed by wound edges previously attached to each other and reducing pressure in the sealed space. The method may also further comprise mechanically pushing the wound edges against each other using the sealant layer, contracting the sealant layer onto a support structure, and/or reducing tissue tension variations along the sealed space. The closed incision may be any of a variety of closed incisions, including but not limited to those closed with sutures or staples. The sutured incisions may be interrupted sutures, running or continuous sutures, and the like.

Further provided herein is a method of applying reduced pressure therapy to a surgically closed area of skin trauma, comprising (a) sizing a collection chamber, a protective layer and a sealant layer to a size of the surgically closed area of skin trauma, (b) forming a seal around said the surgically closed area of skin trauma, (c) activating said collection chamber to deliver reduced pressure to the surgically closed area of skin trauma, and (d) removing the device after at least some re-epithelialization of the surgically closed area of skin trauma. The method further provides a collection chamber wherein the reduced pressure is distributed through the surgically closed area of skin trauma.

A method for treating a surgically closed area of skin trauma using a reduced pressure therapy device comprising the steps of (a) cutting a flexible protective layer to the shape of an area of skin trauma, (b) attaching the cut protective layer to an area of intact skin surrounding the area of skin trauma, (c) cutting a flexible adhesive dressing with an integrated layer of foam to a desired size, said flexible adhesive dressing integrated with said layer of foam in fluid communication with a flexible tubing, (d) placing the dressing over said surgically closed area of skin trauma to form a sealed enclosure, (e) configuring the tubing with an end piece, (f) charging the device, (g) recharging the device as necessary to remove exudates and to restore reduced pressure inside said enclosure, and (h) removing the device after at least some wound re-epithelialization. The method for treating a surgically closed area of skin trauma includes trauma selected from a cut, puncture wound, surgical incision, and any combination thereof.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
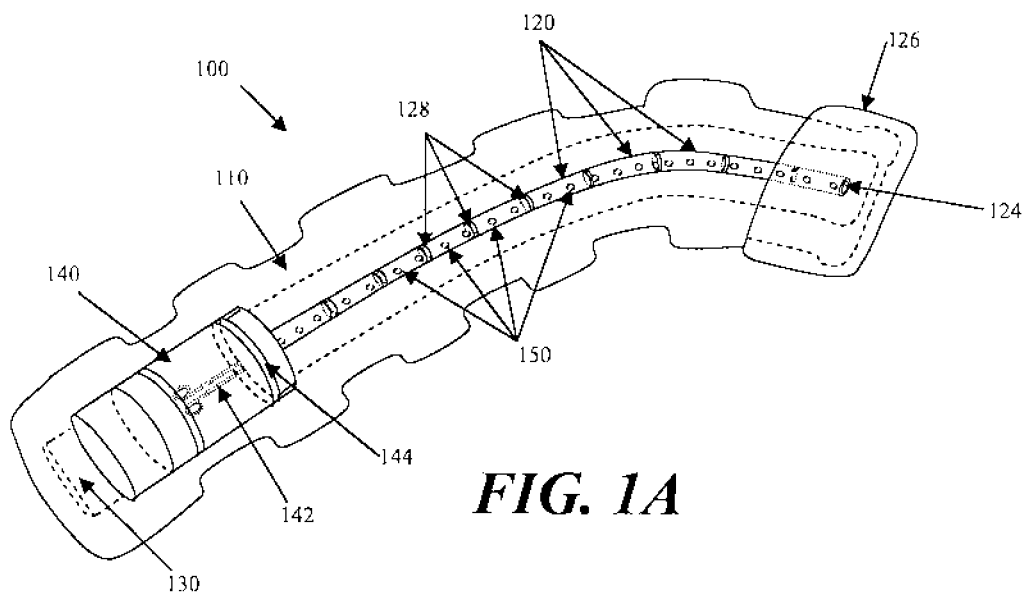
FIGS. 1A and 1B depict one embodiment of a negative pressure therapy device as viewed from the top and from the side perspective.

Infections of surgical incisions and other wounds may result from bacterial growth that occurs in small pockets of fluid collections that may form within the subcutaneous tissues. These small fluid collections lack blood flow and thus may provide inadequate immune function or antibiotic penetration to prevent or treat infection. Once contaminated with bacteria, there can be unfettered growth in these areas. Thus, by reducing the formation of these fluid collections, the risk of a wound infection may be reduced. Although some closure techniques utilize dermal or deep sutures to reduce the formation of these fluid pockets, these sutures may also act as foreign bodies that may increase the risk of wound infection. Furthermore, improper suturing technique may still leave significant dead space under the skin that allows for fluid to collect and eventually become contaminated by bacteria. In addition to wound infection, wound healing may inhibited by excessive tension on the wound. Excessive tension may result from sutures or other wound closure devices that exert focal forces on portions of the incision or wound, and may also lead to increased scarring.

Studies have also demonstrated that a moist wound healing environment may promote more rapid re-epithelialization of wounds by facilitating cell migration toward the wound center, in contrast to current gauze dressings that create a dry wound environment. Moreover, surgical and other wounds undergo of immune cell infiltration, inflammation and subsequent edema. The immune response may be an integral process of wound healing, but the ensuing edema may also be an impediment to healing. Finally, proper healing requires oxygen and nutrients which require adequate perfusion to the incision site which may be impeded by some of the immunological processes.

In one example, a negative or reduced pressure wound therapy system may be used to treat of areas of skin trauma that have been surgically closed, or other types of elongate lacerations or wounds. The negative pressure wound therapy system may comprise a sealant layer and a collection chamber. The sealant layer may be designed such that it can form a seal around a surgically closed area of skin trauma, such as the surgical incision, and form a sealed enclosure or space. In some examples, the sealant layer may comprise a single piece or body, while in other examples, the sealant layer may comprise multiple pieces that may be applied together to form an enclosed space or area. The sealant layer may also comprise a single layer of material, or multiple layers of materials. The seal may be sufficiently air tight so that the pressure in the sealed enclosure or space may be reduced and maintained at a reduced level. The negative pressure therapy system may also comprise a collection chamber that is configured to distribute the reduced pressure applied to the surgically closed incision site along the length of the incision or wound. The negative pressure therapy system may also be used to treat a surgical incision left open to heal by secondary intention, or by delayed primary closure (i.e. third intention). The system may comprise a collection chamber in continuity to a surgical incision that is sealed in a closed system as created by a sealant layer. The collection chamber, when activated, may generate a negative pressure at the surgical incision site to promote healing, remove exudate, and/or reduce infection rates, for example. In some particular examples, the system provided herein may have an elongate configuration and may be sized or configured to conform to the length of the surgical incision. The collection chamber may be integrally formed or pre-attached to a sealant layer, or the collection chamber and the sealant layer may be configured to permit the collection chamber to be positioned under the sealant layer.

In some embodiments, the system further comprises a suction apparatus. When the suction apparatus is used with the system, the suction apparatus may be configured to be in communication with the sealed enclosure or space. The suction apparatus, together with the sealant layer and collection chamber, may form a closed system for treating a surgical incision or other type of wound. The suction apparatus, when engaged, may be used to reduce the level of pressure located inside the sealed enclosure by forcefully expanding the volume of air located within the sealed enclosure. The suction source may be a closed or open system. For example, the suction apparatus may be a syringe, a powered pump, a Venturi system, a forced expansion device, constant force spring device, or a static negative pressure device, or any suitable active or passive suction source. In some embodiments, the suction source may be integrally formed with the collection chamber. In some embodiments, the suction source is connected to the collection chamber through the use of an extension tube.

In some embodiments, the system further comprises a contact layer. The contact layer may be configured to permit fluid communication with the collection chamber. The contact layer may be placed in contact with the surface of the surgically closed area of skin trauma. In some embodiments, the contact layer may only be in contact with the surgically closed area of skin trauma and may not be in contact with the area surrounding the site of trauma. In other embodiments, the contact layer may be in contact with both the area of skin trauma and the area surrounding the area of skin trauma. The contact layer may facilitate the continuity of fluid communication between the collection chamber and the surgical area of skin trauma. In some examples, the contact layer may comprise a porous material or other structure comprising air spaces, including, but not limited to, foam, a stacked mesh matrix, gauze, cotton, a sponge, or any known suitable material in the art. In some embodiments where the contact layer is used, the contact layer may serve as a delivery vehicle for delivery agents. The delivery agents may include, but are not limited to, growth factors, antibiotics, antimicrobial agents, or any suitable delivery agent. In some embodiments, the agents used to improve healing are integrated with the contact layer. In some embodiments, the agents used are integrated or located with the collection chamber.

In some embodiments, the system further comprises a protective layer. A protective layer may be used to surround the surgical area of skin trauma. For example, the protective layer may be attached or adhered to the area of skin surround the area of skin trauma. A pressure sensitive adhesive on the underside of the protective layer may provide the attachment or adherence properties to the skin. A protective layer may also be used to form a seal in combination with a sealant layer. The seal is airtight, or may be semi-permeable or impermeable to water vapor. In some embodiments, the protective layer may be sized to the surgical area of skin trauma such that it fits around the area of skin trauma. In some examples, the protective layer may be cut to size, but in other embodiments, the protective layer may comprise perforations or other pre-defined separation structures to facilitate the sizing. In certain embodiments, the protective layer may have a thin central peel-away strip or layer that may be removed after the protective layer has been placed around the area of skin trauma. In such embodiments, a wider contact layer may be placed over the protective layer. The protective layer may be used to affix the contact layer to the surgical area of skin trauma, and may protect the underlying skin or tissue from trauma associated with removal of the contact layer to access the surgical site. The protective layer can be any known material suitable for protecting the skin surrounding the skin trauma from maceration. The protective layer may comprise any of a variety of foam and/or hydrocolloid materials, including Duoderm® wound care products.

The collection chamber of the static negative pressure therapy system may be configured to distribute the pressure levels applied to the incision site over the length of the surgically closed area of trauma. In some embodiments, the collection chamber may be in a pre-evacuated state prior to being placed on the surgically closed incision area of skin trauma. In such an embodiment, the collection chamber, once in communication with the area of skin trauma, can then be activated to apply reduced pressure to the area of skin trauma. In some examples, the collection chamber comprises a tubular structure. The tubular structure may comprise a rigid tube, for example, a moldable or flexible tube. The tube may comprise a deformable or elastic support that permit the tube to be bent or shaped into a particular configuration while also allowing the tube to holding or biasing the tube in that configuration. For example, the support structure may comprise a wire mesh cage or frame surrounding the tube, coupled to the inner lumen of the tube, or otherwise supporting the tube. In some embodiments, the tube has a wire support structure integrally within the walls of the tube. The support structure may also comprise a moldable plastic material, or the tubing itself may comprise a moldable plastic including. Moldable materials include, but are not limited to, thermoplastics, elastomeric materials, or any suitable moldable material. In some embodiments, the collection chamber may be configured for single use only, while in other embodiments, the collection chamber may be emptied and re-evacuated during use.

In some embodiments, the collection chamber is a flexible tube which comprises one or more corrugated sections. In such an embodiment, the corrugated tubing section may be flexible and can conform to the surface topology of the surgically closed area of skin trauma. The corrugated tubing sections may allow the flexible tubing to conform to the two-dimensional or three-dimension configuration of the wound or incision and allows the tubing to passively adjust in response to changes in the wound configuration as the patient moves or as the wound heals. In some embodiments, the flexible tube may comprise entirely of corrugated tubing, while in other embodiments, the flexible tubing is corrugated tubing sections with discrete collection members or non-corrugated sections located therebetween. In one embodiment, the non-corrugated sections may be rigid, or may be semi-rigid or flexible but with less flexibility than the corrugated sections. Some embodiments may comprise at least one non-corrugated section located within the tubing, while other embodiments may comprise two or more non-corrugated sections located along the tubing. The tubular segments may be connected by corrugated tubes that provide fluid communication along a length of the tubing and/or provide flexibility to the tubing such that the entire collection chamber structure, the rigid non-corrugated sections and the flexible corrugated tubing sections overall permit conformation to the skin or surgical site as it moves. Sometimes, flexible tubing may mitigate the discomfort to the patient or reduce the localized pressure points from the treatment system. In some embodiments comprising both rigid collection sections and flexible sections along the collection chamber, both the flexible tubing segments and the rigid collection sections may be embedded into the sealant layer, coupled to the sealant layer, or integrally formed with the sealant layer. In some embodiments, only the discrete collection members are coupled or embedded into the sealant layer, while the flexible tubing segments are not.

Some embodiments of the system comprise a collection chamber and a sealant layer, where the sealant layer and the collection chamber are in fluid communication with an area of skin trauma. Fluid communication may be provided by a series of openings in the sealant layer and the collection chamber which provide fluid communication between the area of skin trauma and the collection chamber. The openings may be located longitudinally oriented along a length of the collection chamber, with corresponding openings of the sealant layer aligned with the openings in the collection chamber. Fluid, or any other suitable matter, may then be drawn up from the surgically closed area of skin trauma into the collection chamber. When an optional contact layer is employed, the fluid may passes first through the contact layer, and then through the holes connecting the sealant layer and collection chamber. In addition, the series of openings located throughout the collection chamber may allow for the distribution of pressure to the area of skin trauma and reduce or prevent areas of localized pressure or fluid build-up that may be greater in some areas and less in other areas.

In some embodiments, the collection chamber further comprises a one-way flow valve. The one-way flow valve may be used to assist in the emptying of the collection chamber. The one-way flow valve may also be used to re-create the reduced pressure, or pre-evacuated, level of pressure inside the collection chamber. In some embodiments, the one-way flow valve may be used to facilitate both emptying of the collection chamber and re-evacuation of the collection chamber. The one-way flow valve may serves to facilitate the re-evacuation of the collection chamber by facilitating the attachment of a suction source to the collection chamber through the valve and allowing the suction source to remove air molecules from the collection chamber. The suction source may also be used to remove exudate or air from the collection chamber through the use of the one-way flow valve. In some embodiments, a first one-way flow valve is used to empty the collection chamber and a second one-way flow valve is used to re-evacuate the collection chamber. In some embodiments, the one-way flow valve may be integrated with the collection chamber. In some embodiments, the one-way flow valve is attached to a removable plug used to occlude one end of the collection chamber. In some embodiments, a plurality of one-way valves may be provided, with one or more valves located in or associated with the series of openings to reduce backflow of air or material out of the collection chamber or the sealant layer and back into the area of skin trauma. The one-way valves may have any of a variety of configurations, including duckbill or flap valves.

A segmented collection device or other multi-cavity device may be used in place of a single chamber collection chamber in some embodiments. A segmented collection chamber may comprise a first chamber and a second chamber which may or may not be in fluid communication with each other. In one example, the first chamber is in direct communication with the sealant layer whereas the second chamber is in communication with the first chamber. In embodiments where a dual chamber collection chamber is used, one or more of the segments or chambers may be a source of suction. The suction source may comprise a non-powered or passive actuating and regulating mechanism, including but not limited to a spring mechanism such as a constant force spring. The passive actuating and regulating mechanism may be used to apply and maintain a level of pressure inside the sealed enclosure or space between the collection chamber and the sealant layer. In some embodiments, the dual chamber collection chamber comprises a reciprocating mechanism including, but not limited to, a plunger. The plunger may be manually distracted, or may be passively distracted, such as when attached to a constant force spring. In some embodiments, the second chamber expands the volume of air located in a joint volume of space shared between the sealed enclosure and the dual chamber collection chamber. One or segments or chambers may also comprise a powered or active actuating and regulating mechanism.

In some embodiments, the system may also be sized or configured to conform to the length of the surgically closed incision. In some embodiments, the collection chamber conforms to the length of the closed incision area of skin trauma by being stretched to the length of the wound. In such an embodiment, the collection can be made from a hydrocolloid material. Such a material allows the collection chamber to be stretched to a new desired length and remain at that length after the stress causing the change in length has been removed. In such an embodiment, the system may be made from a hydrocolloid or any suitable material. In some embodiments, the system may be shortened to the length of the closed incision. In some embodiments, the system can be cut to the length of the closed area of skin trauma. In such an embodiment, the cut end of the collection chamber may be self sealing upon the application of pressure to the collection chamber. In some embodiments, the collection chamber can be sealed after it has been cut. In some embodiments, the collection chamber can be sealed with an end cap, a plug, an occlusive sealant sheet, an end cap with a one way flow valve, a constant force spring, a reduced pressure system, or any suitable means for sealing the end of the collection chamber. In one embodiment, the structure used to seal the end of the collection chamber that has been adjusted to conform to the length of the skin trauma is configured to resist removal once affixed to the collection chamber. Alternatively, the structure used to seal the end of the collection chamber that has been adjusted to conform to the length of the skin trauma may be a removable structure. In some embodiments, the system includes a series of collection chambers lined up in parallel or serially with each other. In such an embodiment, one or more collection chambers may be removed from the series of collection chambers to accommodate the width of the closed incision area of skin trauma. In other embodiments, one or more collection chambers may be replaced upon filling or clogging.

In some embodiments, the contact layer may be adjusted to conform to the length of the surgically closed area of skin trauma. For example, the contact layer may be lengthened or shortened based upon the length of the closed incision or wound. In some embodiments, the contact layer may be cut to the length of the closed incision. In some embodiments, the collection chamber, the contact layer, and/or the sealant layer may be adjusted to conform to the length of the surgically closed incision. In some embodiments, only the collection chamber is adjusted to conform to the length of the incision before the system is placed on the patient, while in other embodiments, only the contact layer or the sealant layer is adjusted to conform to the length of the surgical incision before the system is placed on the patient. In some embodiments, the collection chamber, the contact layer, and the sealant layer may each be individually adjusted to conform to the length of the incision or wound before being placed on the patient. In some embodiments, the collection chamber, the contact layer, and the sealant layer are integrated together, such that the system is adjusted to conform to the length of the surgically closed incision or wound as a unit.

The system provided herein includes a sealant layer for creating a seal with the surface of the patient. In some embodiments, the seal is air tight. In some embodiments, the sealant layer comprises a flexible impermeable material. In some embodiments the sealant layer is a semi-rigid material. In an embodiment where the sealant layer is a semi-rigid material, the sealant layer may provide tensile support to the surgically closed area of skin trauma. A semi-rigid sealant layer would further alleviate mechanical tension on the surgically closed area of skin trauma as the trauma heals.

In some embodiments, the system provided for herein further includes absorbent beads. The absorbent beads are located in the incision or wound, and/or the collection chamber. In some embodiments, the system may comprise antimicrobial agents. Antimicrobial agents include, but are not limited to, silver, iodine, chlorhexidine or any other suitable antimicrobial agent.

Some of the examples provided herein are configured to create a level of pressure within the sealed enclosure encompassing the surgically closed area of skin trauma. In some embodiments, the level of pressure created is between about 0.001 and about 1 atm. When in fluid communication with the enclosed space under the sealant layer, the level of atmospheric pressure underneath the sealant layer may be reduced to no lower than about 0.001 atm, about 0.005 atm, about 0.01 atm, about 0.05 atm, about 0.1 atm, about 0.2 atm, about 0.5 atm, about 0.7 atm, or about 0.9 atm. In other embodiments, the atmospheric pressure underneath the sealant layer may be reduced to about 0.8 atm or less, but in other embodiments, may be reduced to less than about 0.7 atm, 0.6 atm, about 0.4 atm, about 0.3 atm, about 0.2 atm, about 0.1 atm, about 0.07 atm, about 0.03 atm, about 0.007 atm, or to about 0.003 atm or less.

In some embodiments, the contact layer, the sealant layer and/or the collection chamber may be made from transparent materials. The transparency of the materials may facilitate more accurate placement of the system over the surgical incision or wound by the clinician to more accurately place the system, and/or may permit visualization of the incision or wound with breaking the seal.

Also provided for herein is a method for applying a reduced pressure therapy system to a surgically closed area of skin trauma. The method comprises (a) sizing a collection chamber, a protective layer and a sealant layer to a surgically closed area of skin trauma; (b) forming a seal around the surgically closed area of skin trauma; (c) activating the collection chamber to deliver reduced pressure evenly distributed to the surgically closed area of skin trauma; and (d) removing the system after re-epithelialization of the surgically closed area of skin trauma. Wound re-epithelialization occurs between 2 days and 5 days after the skin trauma has been surgically closed. In some embodiments wound re-epithelialization occurs 3 days after closure. In some embodiments wound re-epithelialization occurs 4 days after closure. In some embodiments wound re-epithelialization occurs 5 days after closure. In some embodiments, wound re-epithelialization occurs earlier than 5 days after wound closure. In some embodiments, wound re-epithelialization occurs earlier than 4 days after wound closure. In some embodiments, wound re-epithelialization occurs earlier than 3 days following wound closure.

Further provided is a method for treating an area of skin trauma using a reduced pressure therapy system, comprising: (a) cutting a protective layer to the shape of an area of skin trauma; (b) attaching the cut protective layer to an area of intact skin surrounding the area of skin trauma; (c) cutting a flexible adhesive dressing with an integrated layer of foam to a desired size, said flexible adhesive dressing integrated with said layer of foam in fluid communication with a flexible tubing; (d) placing the dressing over said surgically closed area of skin trauma to form a sealed enclosure; (e) configuring the tubing with an end piece; (f) charging the device; (g) recharging the device as necessary to remove exudates and to restore reduced pressure inside said enclosure; and (h) removing the device after wound re-epithelialization. In some embodiments the skin trauma is selected from a cut, puncture wound, surgically created incision, or any other wound which is suitable for being closed surgically.

Devices

Figure 1B:
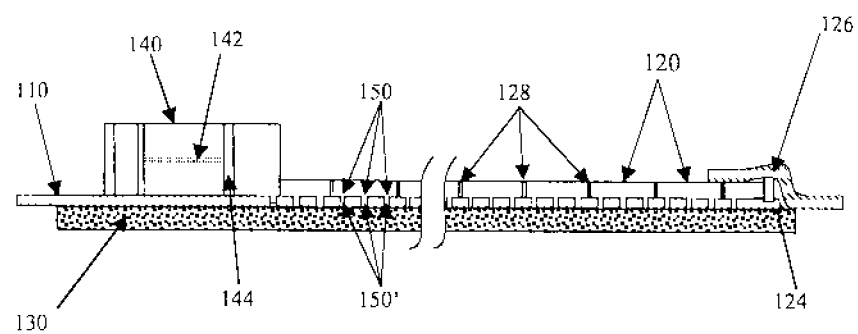

FIGS. 1A and 1B illustrate one embodiment static negative pressure device 100. The device 100 comprises a sealant layer 110 and a collection chamber 120 configured to distribute pressure along a surgical area of skin trauma, such as the length of a surgical incision. In some embodiments, the negative pressure therapy device may include a contact layer 130. The contact layer 130 provides fluid communication between the collection chamber 120 and the area of skin trauma. The contact layer 130 may comprise a foam, mesh, gauze, sponge, particulate matter, a stacked mesh matrix, or any other suitable porous biocompatible material, for example. The contact layer 130 may be put into contact with the surface of the surgically closed area of skin trauma. In some instances, the contact layer 130 may be configured to maintain continuity of the air/fluid spaces through the surgical site, which may reduce the occurrence of isolated fluid or air pockets in the enclosed space formed by the surgical area and the sealant layer 110. In some embodiments, the contact layer may be within the borders the skin trauma surface and not contact, overlap or cover the surrounding tissue area adjacent to the skin trauma. In other embodiments, the contact layer may be placed in contact with the adjacent tissue surrounding the skin trauma, in addition to the region of skin trauma itself. As shown in FIG. 1A, the contact layer 130, the sealant layer 110, and the collection chamber 120 may be coupled or integrated together. In some examples, a pre-coupled or integrated design may permit the device 100 to be placed in contact with the skin trauma surface in one step. In some embodiments, the contact layer is placed in contact with the skin trauma surface. Once positioned, the contact layer is then covered by the sealant layer with an integrated collection chamber to form a sealed enclosure or space. In some embodiments, the sealant layer may be affixed to the area of skin surrounding the trauma area by any suitable materials or mechanisms known to one skilled in the art, including but not limited to, tape, glue, or a suitable biocompatible adhesive product.

Further depicted in FIG. 1A is one example of a suction apparatus 140. The suction apparatus 140 may be configured to create a level of reduced pressure inside of the collection chamber 120. In some embodiments, the collection chamber 120 may be in a pre-evacuated state prior to being positioned on the surface of the skin trauma, while in other embodiments, the collection chamber 120 may be evacuated after positioning, or after coupling to the suction apparatus 140. The collection chamber 120 may be pre-evacuated at the point-of-use or at the point-of-manufacture. In some embodiments, the suction apparatus may be coupled to the collection chamber prior to being positioned on the surface of the skin trauma, and in still other embodiments, the suction apparatus and the collection chamber may be integrally formed. In some embodiments the collection chamber may be sized to the length of the surgically closed area of skin trauma by cutting the collection chamber or by detaching or one or more portions of the collection chamber. In some configurations, the collection chamber may have one or more pre-defined separation zones with reduced thickness to facilitate length reductions. A suction apparatus can then be attached or otherwise used to close the cut or separated end of the collection chamber. FIG. 1A shows the device 100 with a collection chamber 120 in which a suction apparatus 140 comprises with a constant force spring mechanism 142 has been integrated with the collection chamber 120. When the constant force spring mechanism 142 of the suction apparatus 140 is engaged, the slidable seal or reciprocating mechanism 144 may be drawn back to create and maintain a constant level of pressure inside the sealed enclosure. In FIG. 1A, the device 100 has been sized to the length of a wound by cutting one end 122 of the collection chamber 120. FIG. 1A further depicts the non-suction apparatus end 122 being occluded by an end plug 124. The device is further sealed in FIG. 1A using an end sealant structure 126. The non-suction apparatus end 122 and/or the end plug 124 may be configured to detachable or non-detachable. For example, a glue may be used to irreversibly attach the end plug to the apparatus end 122.

In some embodiments, the length of the collection chamber may be adjusted based upon the length of the surgical incision or wound. The length of the surgical incision or wound may be generally linear or may be non-linear. In some examples, the length of the collection chamber is about the length of the surgical wound, while in other examples, the collection chamber length may be about +10%, about +20%, about +30% or more, about −10%, about −20%, or about −30% or less than the length of the surgical wound. Although generally elongate surgical wounds are contemplated, in other examples, surgical wounds with non-elongate configuration may also be treated. In some further examples, branching or stellate surgical wounds may be treated, using one or more devices. In other examples, the surgical wound or incision may be characterized as the affected length of a partially dehisced surgical wound. In examples where the surgical wound comprises a partially dehisced surgical incision, the sealant layer and/or contact layer may be configured to seal or cover the dehisced segment, or the entire wound or incision. Exemplary methods for treating non-elongate wounds are described later below. In some examples, the collection chamber per cm length, may have a volume in the range of about 100 mm3 to about 10,000 mm3 or more, sometimes about 500 mm3 to about 7,000 mm3, and other times about 1,000 mm3 to about 5,000 mm3

The collection chamber 120 may be in fluid communication with the skin trauma site through the contact layer 130 of the device 100. In some examples, the collection chamber 120 and the sealant layer 110 are integrally formed. As depicted in FIG. 1B, the collection chamber 120 may comprise a plurality of openings 150 that may align or correspond to a plurality of openings 150' in the sealant layer 110 to provide fluid communication between the skin trauma and collection chamber 120 through the contact layer 130 and the sealant layer 110. The series of openings 150 and 150' may permit distribution of the pressure changes applied to the area of skin trauma across the length or region of the skin trauma. The spacing, size or shape of the openings 150 and 150' along the collection chamber 120 and/or the sealant layer 110 may be uniform or non-uniform. In other embodiments, the collection chamber 120 and the sealant layer 110 may comprise separate structures that are configured for coupling. To facilitate alignment of the collection chamber openings 150 with the openings of the sealant layer 110, the adjacent surface of the collection chamber 150 and/or the sealant layer 110 may comprise an adhesive or slip-resistant surface. In other embodiments, the collection chamber openings 150 and/or openings in the sealant layer 120 may form complementary interfit to facilitate alignment. For example, the collection chamber openings 150 and/or the sealant layer openings 150' may protrude into the opening in the corresponding structure. In still other embodiments, the collection chamber openings 150 and the sealant layer openings 150' may comprise complementary sealable snapfit.

In some examples, the collection chamber may comprise an elastically or plastically deformable material or a bendable configuration. This may permit the collection chamber to conform to the contours of a surgically closed area of skin trauma, and may permit the collection chamber to exhibit at least some conformational change in response to body movement. In one example depicted in FIGS. 1A and 1B, the collection chamber 120 comprises regions or zones of flexible ribbing 128 along the length of the collection chamber 120. The ribbing 128 allows the collection chamber 120 to be shaped and molded by the user and further maintains the user defined configuration. The portions of the collection chamber 120 between the flexible ribbing 128 may be rigid, semi-rigid or flexible. In some further examples, a collection chamber may also be configured to at least partially rotate in addition to bending. In certain examples, different sizes or configurations of openings may be provided around the circumference of the collection chamber and may be selected for use by rotation. The unused opening may be sealed by applying a sealant layer over the unused openings. Alternatively, the openings may be pre-sealed and the selected seals may be utilized by removing the pre-attached seal(s) from them.

Figure 2:
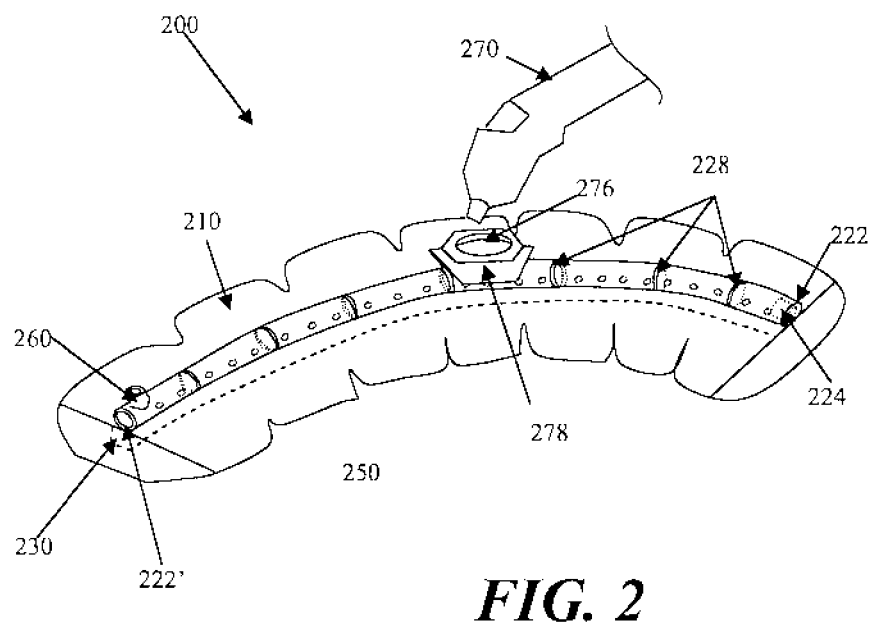
FIG. 2 depicts an embodiment of a negative pressure therapy device as viewed from above in which the device is designed to be emptied and re-evacuated.

FIG. 2 shows another embodiment of a negative pressure therapy device 200 in which the device 200 is configured to be re-evacuated or recharged. The device 200 comprises an integrated contact layer 230, sealant layer 210 and collection chamber 220. The contact layer 230 may be placed in contact with the surface of the skin trauma and a seal may be formed between the skin surrounding the skin trauma using the sealant layer 210. The collection chamber 220 may be integrated with the sealant layer 210 and is in fluid communication with the contact layer and the enclosed surgical site through a series of openings 250 in the collection chamber 220 and the contact layer 230, but in other examples, the collection chamber and the sealant layer may be separated components that may be attached using adhesive or mechanical mechanisms. With separate collection chambers and sealant layers, the alignment of the collection chamber openings and the sealant layer openings may be facilitated by configuring either the collection chamber openings and/or the sealant layer openings with complementary interfit designs. In one alternative embodiment, the base sealant layer may lack pre-formed openings, but the collection chamber openings may comprise sharpened or penetrating structures to permit formation of sealant layer openings when the two components are coupled together.

The collection chamber 220 may be in a pre-evacuated state wherein a level of reduced pressure is already present inside. Alternatively, the collection chamber 220 can be at atmospheric pressure when placed on the patient, and a reduced level of pressure can be created in the collection chamber using an external evacuator device 270, such as a durable medical equipment evacuator. The external evacuator device 270 may be positioned in an opening 276 of an evacuator fitting 278 on the collection chamber 220. The evacuator fitting 276 is in fluid communication with the collection chamber 220. The evacuator fitting 276 may be configured as a one-way flow valve that allows air molecules or other materials to be removed from the collection chamber 220 while resisting entry of air molecules or other materials into the collection chamber. In the particular examples illustrated in FIG. 2, the collection chamber 220 comprises flexion regions 228 with ribbing, but in other examples, a substantial length of the collection chamber comprises a flexible material.

FIG. 2 also depicts a collection chamber 220 with one end 222 occluded with an end plug 224. The other end 222' of the collection chamber may be fitted with a one-way flow valve 260. Thus, the device 200 may comprise a separate one-way flow valve 260 for facilitating the emptying of the collection chamber 220 when the collection chamber 220 is filled with exudate or other matter. Once the collection chamber 220 has been emptied, the collection chamber can then be re-evacuated using an external evacuator 270 introduced through the opening 276 of the evacuator fitting 278. In some embodiments, the one-way flow valve 260 and the means for evacuating the collection chamber 220 are the same structure. In some embodiments, the one-way flow valve and the means for evacuating the collection chamber are two different structures, as shown in FIG. 2. FIG. 2 also shows a device 200 with a moldable collection chamber 220.

Figure 3:
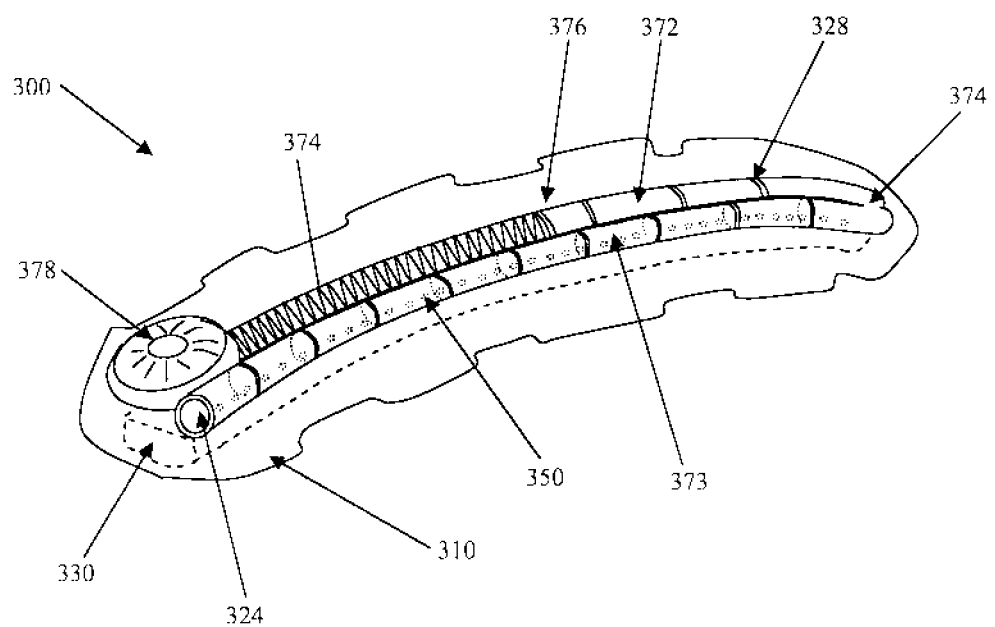
FIG. 3 depicts an embodiment of the negative pressure therapy device as viewed from above in which the collection chamber is a segmented collection chamber.

Another example of a negative pressure therapy device 300 is shown in FIG. 3. The negative pressure therapy device 300 may comprise a multi-chamber collection system 370, comprising a first chamber 372 and a second chamber 373. The multiple chambers may be connected, or may be separate. In FIG. 3, for example the first and second chambers 372 and 373 may be in fluid communication with each other at an interconnecting opening 374. The first chamber 373 of the dual chamber collection chamber 370 has a series of openings 350 that configured to provide fluid communication with the contact layer 330 of the device 300. The second chamber 372 of the dual chamber collection chamber 370 can be fitted with a reciprocating mechanism for regulating pressure. In FIG. 3, the second chamber the reciprocating mechanism is shown as a spring 374 attached to a spring housing 378 on the end of the dual chamber collection chamber 370 opposite to the sealed end with end plug 324. The spring creates a moving seal 376 through the use of a plunger like apparatus. The moving seal 376 self-regulates changes in pressure in the dual chamber collection chamber 370 and moves in response to these changes.

Figure 4:
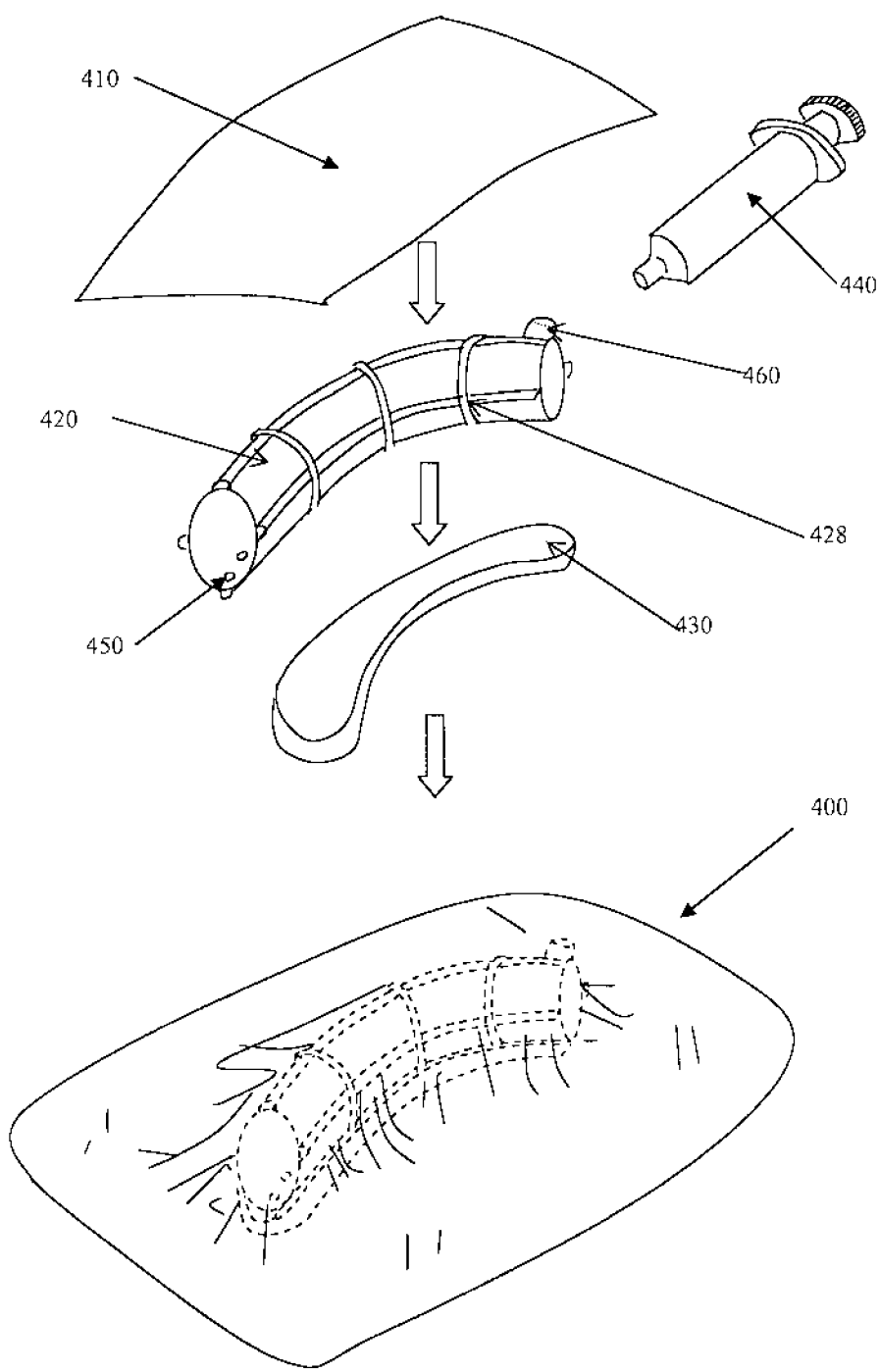
FIG. 4 depicts an embodiment of the negative pressure therapy device in which an occlusive layer is placed over the collection chamber.

FIG. 4 illustrates another embodiment of a negative pressure therapy device 400, in which contact layer 430, the collection chamber 420, and the sealant layer 410 of the device are not integrated and the sealant layer 410 is placed above or over the collection chamber 420 and contact layer 430. In this embodiment, the contact layer 430 is placed in contact with the surgically closed area of skin trauma. A moldable collection chamber 420 with ribbing 428 to may be used to manipulate configuration of the chamber 420 for contact and coverage with the contact layer 430. A series of openings 450 located in the collection chamber 420 provides for fluid communication between the contact layer 430 and the collection chamber 420. The collection chamber 420, once in contact with the contact layer 430, may then be evacuated through the use of suction apparatus 440. The suction apparatus can be a syringe, a powered pump, or a forced expansion device. The suction apparatus 440 is preferably in fluid communication with the collection chamber 420 through a one-way valve 460. After the collection chamber 420 is evacuated, a sealant layer 410 can then be placed over the collection chamber 420 and the contact layer 430 to form a sealed enclosure with the wound.

Figure 5:
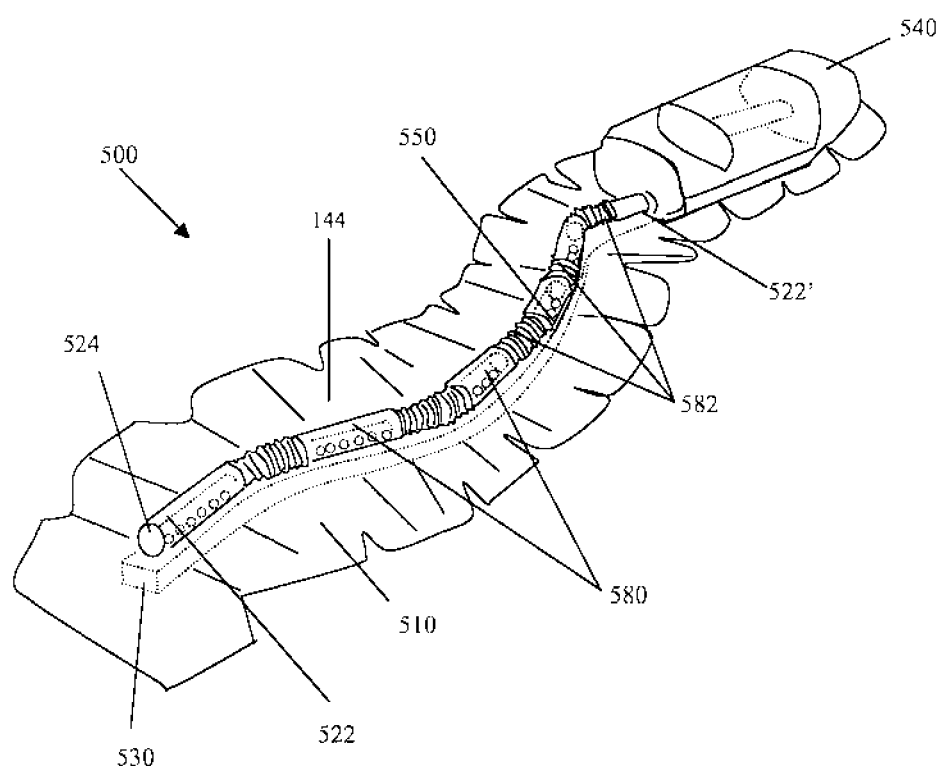
FIG. 5 depicts an embodiment of the negative pressure therapy device in which the collection chamber comprises corrugated tubing segments interspersed with discrete collection members.

FIG. 5 depicts another embodiment of a device 500, in which the collection chamber 520 comprises corrugated tubing segments 582 with discrete collection members 580 interspersed throughout the collection chamber 520. One end 522 of the corrugated tubing is sealed with an end plug 524 or other closed configuration. The other end 522' of the device 500 may be coupled or integral with a suction source 540, such as a constant force spring, a powered suction pump, a durable medical equipment evacuator, or any suitable suction source. The contact layer 530 of the device 500 is integrated with the sealant layer 510 and the collection chamber 520 in FIG. 5. Once placed on the patient, the corrugated tubing segments 582 allow the collection chamber to conform to the surface topology of the patient. This embodiment of the device allows the device to move with the patient. The corrugated tubing segments allows for significant expansion and compression of the underlying skin. In an embodiment where the collection chamber is a corrugated tube with discrete collection members, the discrete collection member 580 are in preferably fluid communication with the contact layer 530 and skin trauma surface through a series of discrete openings 550.

In some embodiments, an elongate reduced pressure therapy system may be applied along the length of an elongate wound with wound edges that may be approximated. The elongate reduced pressure therapy system may also be used with incisions already closed by sutures, staples or adhesives, for example. In some instances, the use of a reduced pressure therapy system on a closed incision may provide more uniform force distribution along an incision, by exerting additional closure forces against tissues not immediately contacting a suture or staple, for example. A negative pressure therapy system, in some instances, may also resist separation of the wound edges. In some instances, the negative pressure therapy system may resist stretching of the newly formed connective tissue, which may reduce the extent of scarring. In some examples, by applying a sealant layer and reducing the pressure, the approximation of the wound edges may be further augmented by collapsing the potential space between the edges. In some particular embodiments, the wound treatment system may comprise a negative pressure system that is configured to provide both mechanical tension reduction and reduced pressure effects on the incision or wound. The reduced pressure effects may or may not include the displacement of the wound edges toward each other by reducing the pressure of the space between the wound edges and/or from pushing or pulling by the sealant layer as the sealant layer is contracted around the support. A reduced pressure therapy system may also comprise an elastic sealing layer or a sealing layer configured with one or more elastic members. In use, the sealant layer may be attached or adhered to one side of the incision or wound and then stretched and attached to the other side of the incision or wound. Once in place and with the stretching force relieved, the sealant layer or its elastic member may exert opposing forces on each side of the wound to augment the edge approximation and draw the incision or wound edges together. In some examples, the elastic members may be oriented in a transverse position to the longitudinal orientation of the incision or wound, but in other examples, the elastic member may be oriented in multiple directions. The sealant layer or the elastic member may comprise a material such as silicone rubber, polyisoprene or other elastomeric material which possesses a sufficient restoring force to pull tissue together when adhered to opposing incision or wound edges in a stretched configuration. In some examples, one or more elastic members may be applied or attached to the sealant layer after the sealant layer has been applied to the incision site or wound site.

Figure 6A:
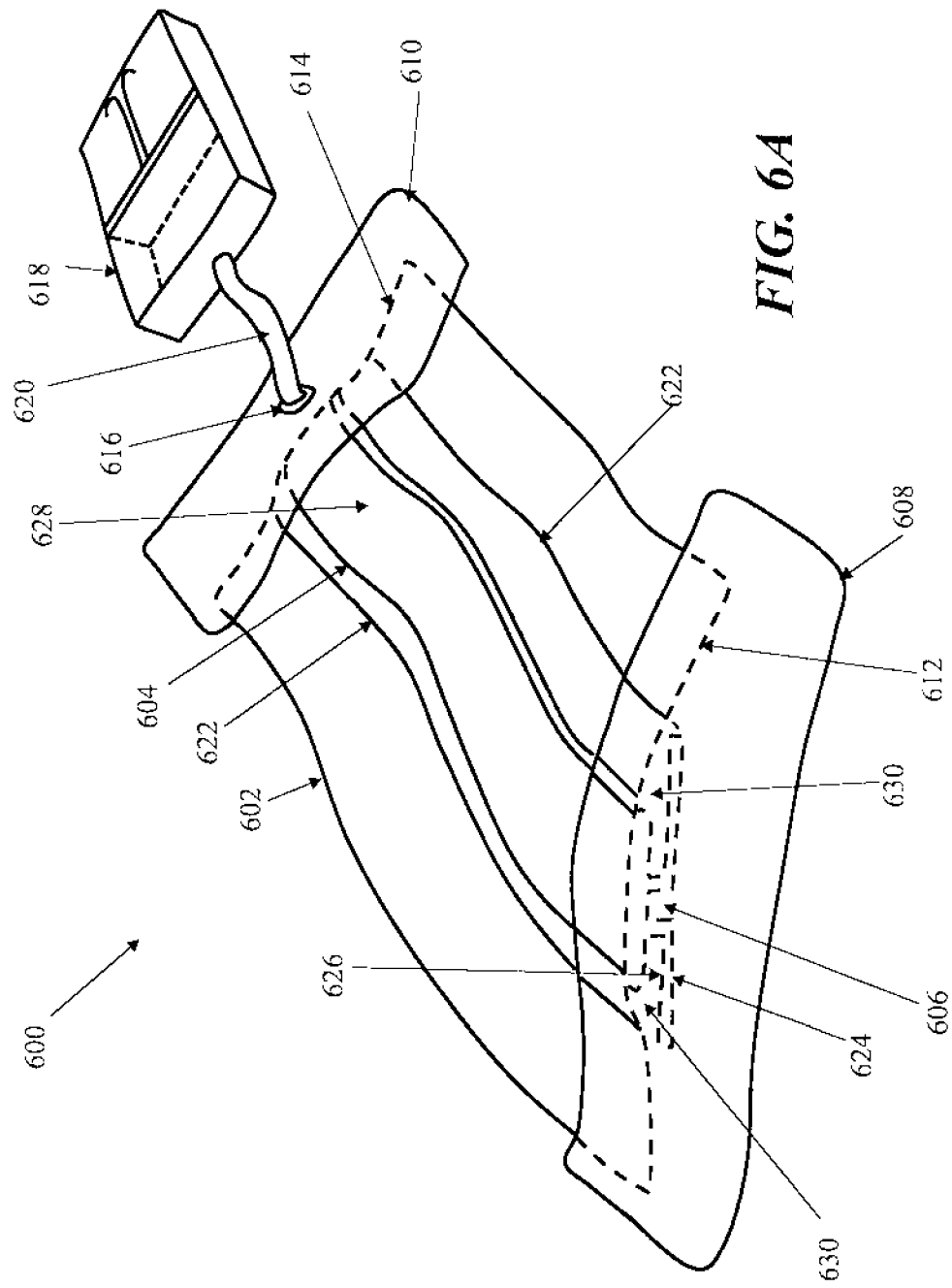
FIG. 6A is a perspective view of another embodiment of a negative pressure therapy device.
Figure 6B:
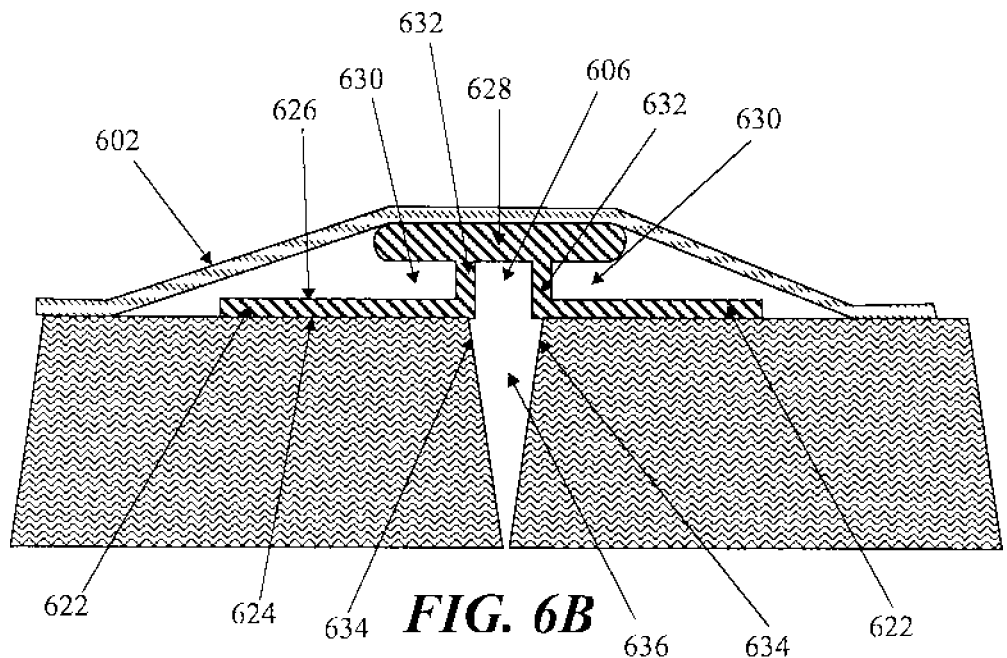
FIGS. 6B and 6C are axial cross-sectional views of the device in FIG. 6A, before and after the application of reduced pressure, respectively.
Figure 6C:
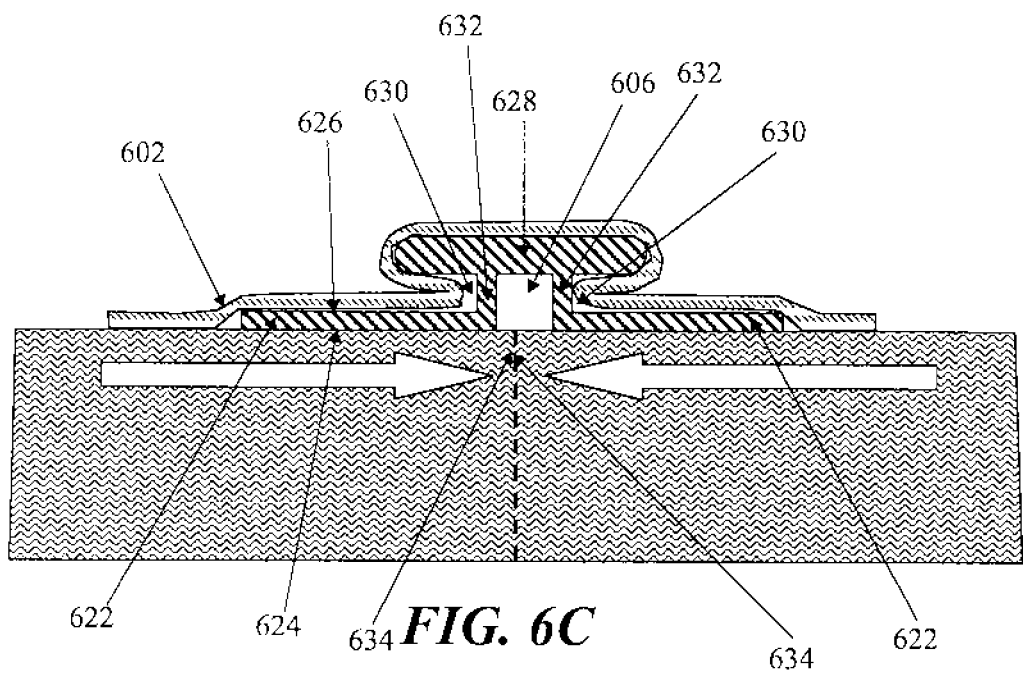

FIGS. 6A to 6C depict another example of a wound treatment device 600 comprising a sealant layer 602 and an elongate support 604. The elongate support 604 may be configured with an elongate central channel 606 that may be placed along or over an incision or elongate wound. In some configurations, the device 600 may comprise multiple channels in direct communication with the elongate wound. In this particular example, the elongate central channel 606 has an open channel configuration that is exposed to the incision or wound along a portion if not all of its longitudinal length, but in other examples, the elongate channel 606 may have a generally closed configuration with a plurality of longitudinally arranged openings along a segment of the channel or the entire channel. An open channel or a plurality of longitudinally arranged openings may permit the application of reduced pressure along a length of the wound while possibly reducing the risk that clogging or transient opposition of tissue surfaces may affect the distribution of pressure reduction and/or fluid suction. In some examples, the channel, or the segment of the channel in communication with the incision or wound, may have a length of at least about 1 cm or more, 3 cm or more, sometimes about 10 cm or more, and other times about 20 or about 50 cm or more. In some examples, the device 600 may comprise a length of about 70 cm, 100 cm or even 150 cm, which may be cut or shortened to a smaller length. In some embodiments comprising a flexible, bendable and/or moldable support 604, the support 604 and/or sealant layer 602 may be provided in the form of a roll or a folded form, which is then dispensed and cut as needed. The device 600 (or other devices described herein) may be used to treat any of variety of incisions or wounds, but in some specific examples may be used to a variety of elongate incisions or wound, including but not limited to linear or curvilinear incisions or wounds. These wounds may include but are not limited to any of a variety of traumatic lacerations or cuts, sternotomy incisions, laparotomy incisions, perineal prostatectomy incisions, vein harvesting incisions, C-section incisions, and the like.

In use, the elongate central channel 606 may be positioned along an incision or elongate wound and then secured or sealed by placing the sealant layer 602 over the incision and support 604. The sealant layer 602 and the support 604 may be integrally formed or pre-attached to each other, such that the sealant layer 602 and the support 604 may be applied to an incision or wound in a single step. In some examples, the sealant layer 602 may have a size and configuration to permit complete sealing of the entire perimeter of the incision and the support 604, but in other examples, one or more accessory seals 608 and 610 may be used. The sealant layer 602 may comprise an adhesive on one or more surfaces. In FIG. 6A, for example, adhesive may be provided along the lateral regions the undersurface of the sealant layer 602, leaving a strip or middle section of the sealant layer 602 free of adhesives. In this particular example, end seals 608 and 610 may be used to facilitate sealing about the ends 612 and 614 of the sealant layer 602, but in other embodiments, accessory seals may be used anywhere to provide additional sealing.

In some examples, the sealant layer, support, and/or one or more accessory seals may be pre-configured with a connector or port which may be used to coupled the device 600 to a reduced pressure source. In the particular example in FIG. 6A, one of the end seals 610 is pre-configured with a connector 616 that may be used to attach a suction device 618 using an optional connector tube 620. In other examples, the suction source or a connector tube may be configured to pierce and form an aperture through the sealant layer or accessory seal. In still other examples, the suction device 618 may be integrally formed with the end seal, sealant layer and/or support 604.

As shown in FIG. 6B, the support 604 may optionally comprise one or more side flanges or flaps 622 to one or both sides of the elongate channel 606. Each of the side flaps 622 may have a width (or dimension transverse to its longest dimension) in the range of about 2 mm to about 50 mm or more, sometimes about 10 mm to about 40 mm, and other times about 20 mm to about 30 mm The side flaps may have an average thickness in the range of about 0 5 mm to about 5 mm or more, sometimes about 0.75 mm to about 3 mm, and other times about 1 mm to about 2 mm The thickness of the side flap may or may not be uniform, and in some examples, the thickness may taper or reduce in a central to peripheral direction, or vice versa. The side flaps 622 may comprise the same or different material as the material about the elongate channel 606. In some embodiments, the support 604 and/or the side flaps 622 may be rigid, semi-rigid or flexible, and may comprise silicone, urethane, or the like, and may or may not comprise a coating. For example, one or more sections of the support 604 may comprise an ant-infective coating, including but not limited to a silver alloy or chlorhexidine coating. The side flaps 622 may or may not comprise an adhesive on its tissue contacting surface 624 and/or its sealant layer contacting surface 626. In some examples, the support 604 may further comprise a cap structure 628. The cap structure 628 may be located on the upper surface of the elongate channel 606 and may be configured to project to one or both sides of the elongate channel 606. The cap structure 628 may project anywhere from about 0 mm to about 15 mm or more, sometimes up to about 5 mm, and other times up to about 10 mm In some examples, one or more elongate side channels 630 may be formed between the cap structure 628 and the side flanges or flaps 622. The cap structure 628 may comprise rounded edges or surfaces, which may or may not reduce the risk of puncturing or damaging the sealant layer when contracted onto the support 604. In some examples, an accessory seal, or a sealant layer configured with regions of greater thickness, puncture resistance, or other reinforcement may be positioned about the support 604. The side flaps 622 and/or the cap structure 628 may or may not have a symmetrical configuration and/or size with respect to the elongate channel 606. In some configurations, one or more openings may be provided in the walls 632 between the central channel 606 and the side channel(s) 630, but in other configurations, communication between the central channel 606 and the side channel(s) 630 may only occur about the ends of the support 604 where the sealant layer 602 may provide a common space or pocket where it may not be adhered to the skin.

As shown in FIG. 6C, when reduced pressure is applied to the device 600, the sealant layer 602 may collapse around or into the support 604. For example, sections of the sealant layer 602 may be pulled or pushed into the elongate side channels 630. In other examples, the support 604 may comprise any of a variety of indentations, openings, grooves, channels which may permit contraction of the sealant layer 602 to the support 604, either with suction or by mechanical structures such as a clamp or pushrod, drawstring or any other complementary structure that may be attached or coupled to tighten the sealant layer 602 to the support 604. In some instances, this contraction of the sealant layer 602 may or may not draw the wound edges 634 closer together. The application of reduced pressure may also reduce the size or eliminate the gap 636 between the wound edges 634.

In addition to the support, the wound treatment system may also comprise one or more elastic elements incorporated or attachable to the sealant layer. For example, elastic bands or threads may be provided in the sealant layer in addition to the elastic properties of the support, if any. In some configurations, the elastic bands or threads may have a uniform orientation, but in other configurations, the elastic bands may be oriented in multiple directions. In some instances, the support may also comprise an elastic material or structure (e.g. a spring) which may be configured to further mechanically bias the wound tissue or edges in a particular direction. In some instances, the spring may comprise an attachable clip, which is optionally used with the support to provide additional force with elastic supports, or the contracting force with rigid supports.

Figure 7:
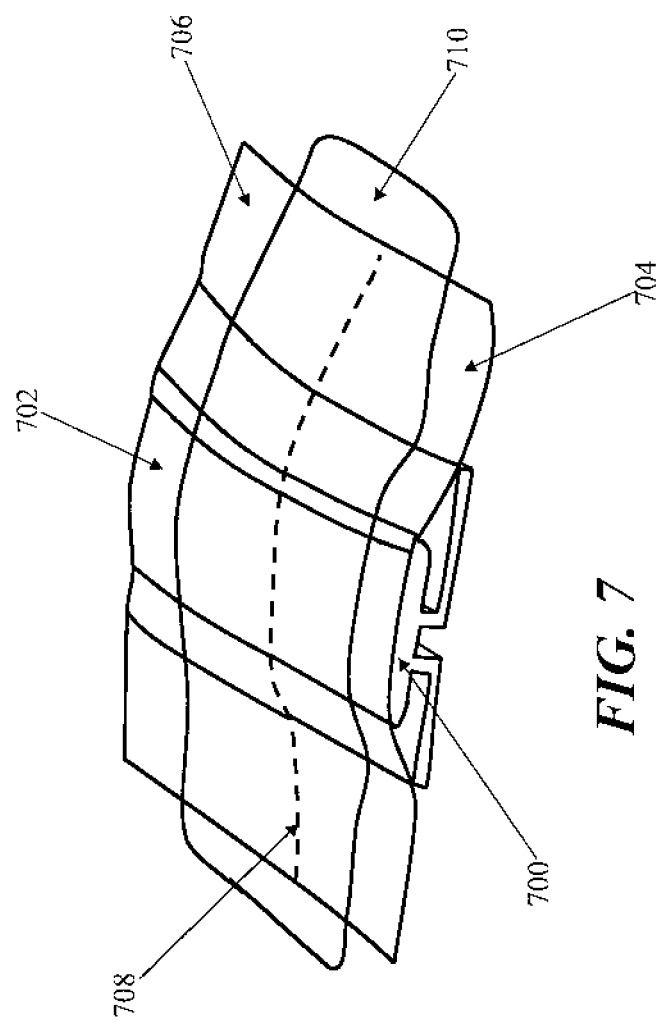
FIG. 7 is a schematic perspective view of two wound coverings joined together.

In some examples, the reduce pressure wound therapy system may be used to treat incisions or elongate wounds that may be longer than the length of the device that is available. In such situations multiple devices, supports and sealant layers may be arranged in an independent or an overlapping configuration to treat larger wounds. In FIG. 7, for example, two separate supports 700 and 702 and sealant layers 704 and 706 are positioned end-to-end and the junction region 708 is covered with a third sealant layer 710. Use of a third sealant layer 710 may be useful, for example, where the support and sealant layer are supplied or manufactured in an integral or pre-attached configuration. Although the ends of the supports 700 and 702 and the sealant layer 704 and 706 are depicted as touching at the junction region 708, in other examples, partial or full gaps may be provided between supports and/or sealant layers. In addition to the serial configuration depicted in FIG. 7, the supports and/or sealant layers may also be arranged in a parallel fashion. In other examples, a third sealant layer need not be used, as one sealant layer may be overlapped over another where the sealant layer extends past the end of it associated support. In other examples, multiple sealant layers or supports may be provided and used with a lesser number of supports or sealant layers, respectively. Also, more than one suction device may be used with longer or larger support or sealant layers.

Figure 8:
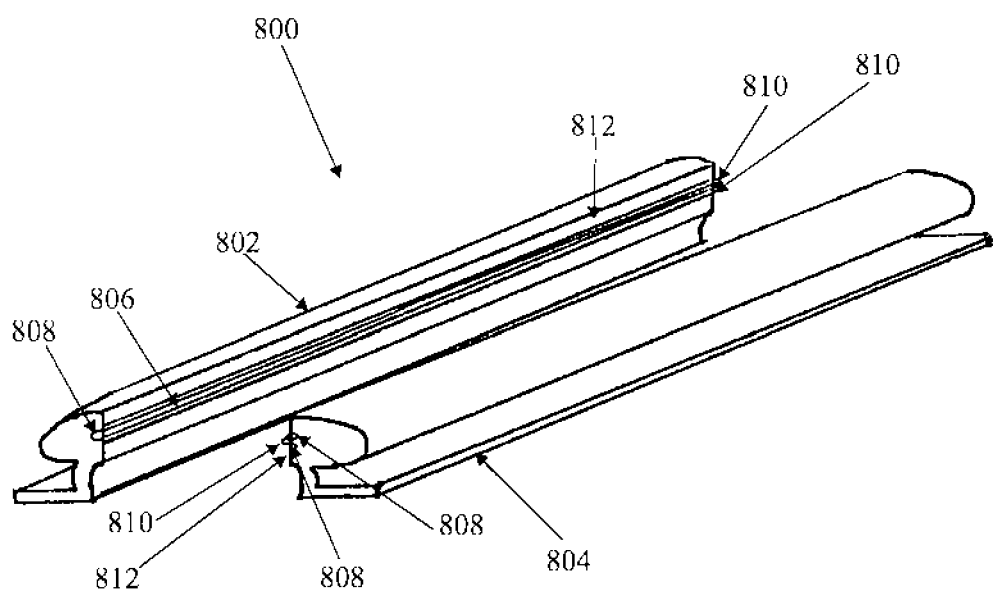
FIG. 8 depicts another embodiment of the negative pressure therapy device, comprising a split support.

In addition to multiple supports that may be arranged in a parallel and/or serial fashion, in some embodiments, the supports themselves may comprise multiple sections that are joined together to form a complete support. In FIG. 8, for example, a support 800 comprise two elongate support segments 802 and 804 which are configured to be generally joined along their longitudinal lengths at a coupling interface 806. A support 800 comprising separate longitudinal segments 802 and 804 may be used to separately attach each segment 802 and 804 to one edge of an incision or wound (e.g. by adhesives or suturing) and are then joined together to approximate the wound edges. In some instances, separate joinable components may be easier to attach to the skin than a unibody support. The longitudinal segments 802 and 804 may be rigid, semi-rigid or flexible, and although the segments 802 and 804 are depicted as each contributing about 50% of the structure, e.g. generally symmetrically split except for possibly the coupling interface. In other examples, however, the longitudinal segments may be asymmetrically split. The coupling interface 806 depicted in FIG. 8 comprises a complementary set of grooves 808 and ridges 810 located along the longitudinal inner surface 812 of each segment 802 and 804, but any of a variety of coupling interfaces 806 may be used, including other snapfits. Other locking interfaces, mechanisms or structures may include but are not limited to resealable adhesive layers, slide locks, hinge clamps, clips, locking pins with lockable lumens, zippers, elastic binding bands, and the like. In some examples, structures that may be used to contract the sealant layer into a unibody support may also be used to contract the sealant layer into a multi-segment support and/or to couple the segments of a multi-segment support together.

Figure 9A:
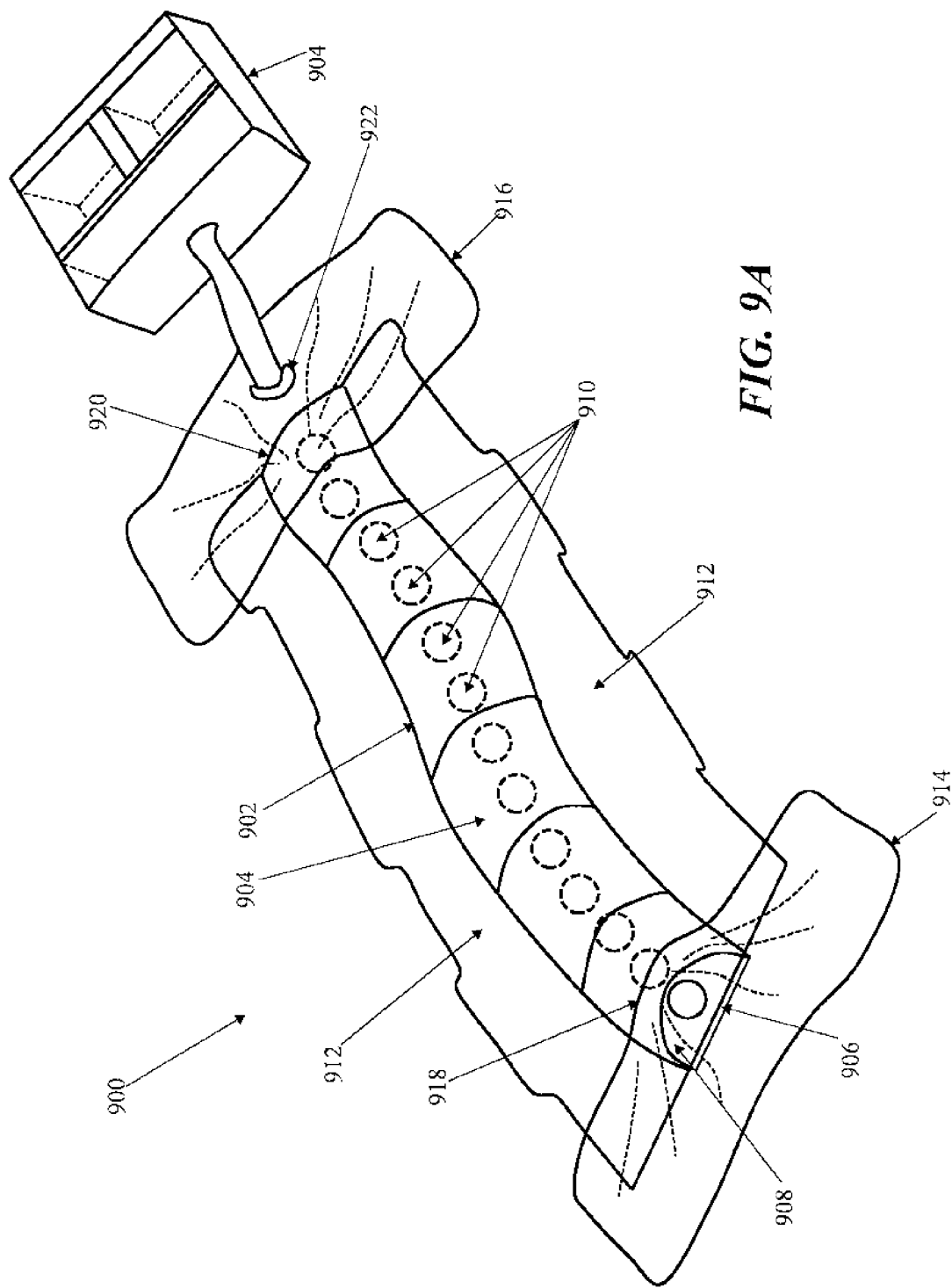
FIG. 9A is a perspective view of another embodiment of a negative pressure therapy device comprising an elastic collection channel.

FIG. 9A depicts one example of a negative pressure therapy system 900 comprising an elastic support 902 and an optional suction system 904. An optional contact layer 906 may be provided under the elastic support 902. The elastic support 902 is configured with one or more longitudinal conduits 908 or channels. The conduit or channel may be fully enclosed or may be at least partially open. The conduit 908 in FIG. 9 has a closed configuration with a plurality of apertures 910 to permit air or fluid communication with the underlying wound or incision. In this particular example, the lateral flaps 912 of the elastic support 904 may comprise an adhesive, which may be used to at least seal a portion of the conduit 908 and the external space, if any, between the incision or wound and the apertures 910. In some other examples, the lateral flaps 912 may extend to one or both ends of the support, but in the example, depicted in FIG. 9A, end seals 914 and/or 916 may be used to facilitate sealing about the ends 918 and 920 of the support 902. As mentioned previously, at least one of the end seals 916 may be provided with a connector 922 for attachment of the suction system 904, but in other embodiments, the connector may be located on the elastic support 902. In still other examples, a large sealant layer may be used to cover a larger portion if not all of the support, and with or without a protective layer. For example, some embodiments of the elastic support may comprise segmented non-sealing lateral flaps which are configured to elastically bring wound edges together. The segmentation may facilitate the application of the elastic support in a sectional manner, but may or may not provide sealing ability, such that a sealant layer applied over the elastic support may be used to provide a sealed space about the support.

Figure 9B:
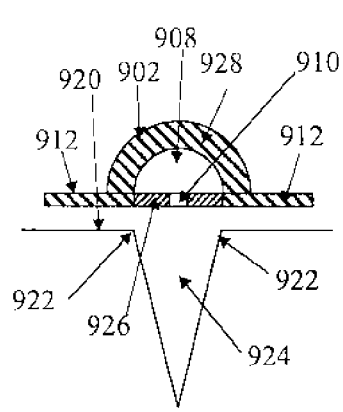
FIGS. 9B to 9D are schematic cross-sectional views of the device in FIG. 9A before, during and after stretching, respectively.
Figure 9C:
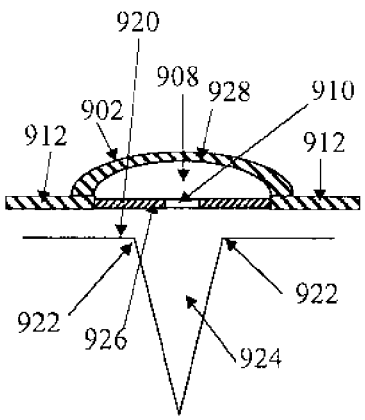
Figure 9D:
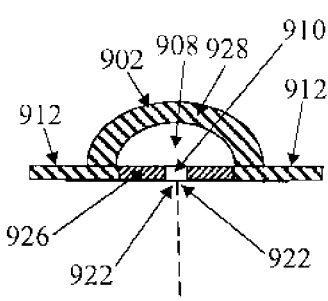
Figure 9E:
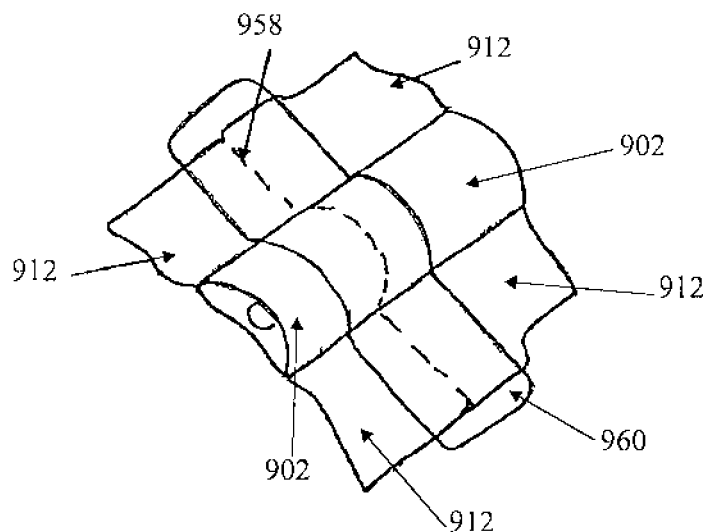
FIG. 9E is a schematic perspective view of two negative pressure therapy devices joined together.

Referring to FIGS. 9B to 9D, in use, the flaps 912 of the elastic support 902 may be elastically stretched or pulled away from each other and applied in its stretched state to the incision or wound such that each flap 912 is adhered to the skin surface 922 to a respective edge of the incision or wound. In some procedures, the support 902 may be sufficient stiff or rigid such that a substantial longitudinal length of the flaps 912 can be stretched, but in other configurations, a smaller portion of the flaps 912 may be pulled away, which may facilitate the application of the support to non-linear incisions or wound by permitting adherence or attachment of the support section-by-section. Once adhered to the skin surface 920, the stretching or deformation force may be relieved, and the elasticity or bias in the support 904 may push the wound edges 922 toward each other. Once fully sealed, the suction source 904 may be activated to reduce the pressure in the conduit 906 and/or to remove air or fluid from the incision or wound, which may or may not further reduce the gap 924, if any, between the wound edges 922, in addition to providing a reduced pressure to enhance healing and/or to evacuate potential fluid pockets. FIG. 9E depicts how two elastic supports 902 with flaps 912 may be positioned serially or in an end-to-end fashion to treat incisions or wounds having a longer length by covering the junction 958 with an accessory seal 960. As noted previously, although the ends of the supports 902 and their flaps 912 are depicted as touching at the junction region 958, in other examples, partial or full gaps may be provided between supports and/or their flaps.

Figure 10A:
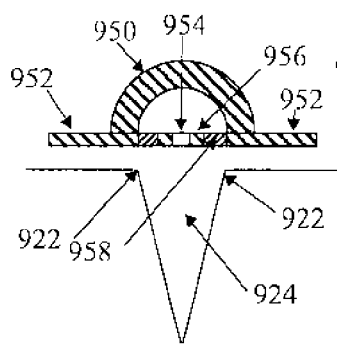
FIGS. 10A to 10C are schematic cross-sectional views of another negative pressure therapy device with reinforced apertures, before, during and after stretching, respectively.
Figure 10B:
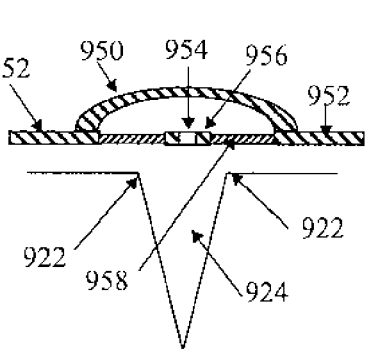
Figure 10C:
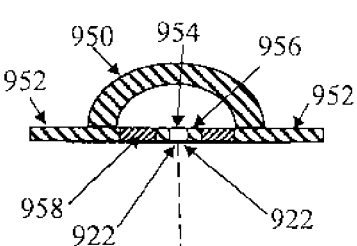
Figure 11A:
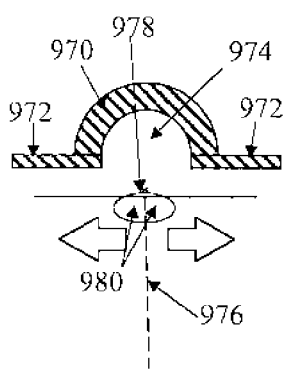
FIGS. 11A to 11C are schematic cross-sectional views of another negative pressure therapy device comprising an open longitudinal channel, before, during and after stretching, respectively.
Figure 11B:
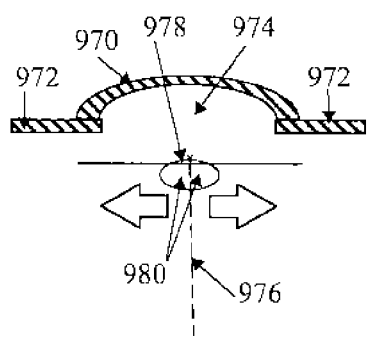
Figure 11C:
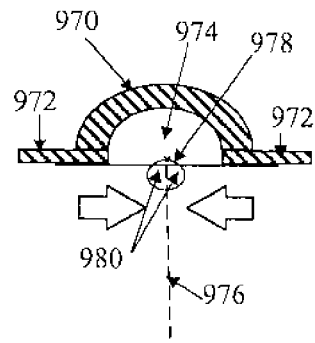

The elastic support may comprise any of a variety of configurations. As depicted in FIGS. 9B to 9D, the elastic support 902 may comprise an elastomeric member 926 which may augment the elastomeric properties, if any, of the flaps 912 and/or wall 928 of the conduit 908. As further illustrated, the apertures 910 of the elastic support 902 may be provided directly in the elastomeric member 926, and in some configurations the apertures 910 may also deform in shape when force is applied to the flaps 912. FIG. 10A to 10C depicts another embodiment of an elastic support 950 with flaps 952, wherein the apertures 954 are provided in a non-elastic structure 956. Thus, when the elastomeric member 958 is stretched, the apertures 954 maintain the same configuration. The non-elastic structure 956 may have any of a variety of configurations, including rings or frames, and may form either a partial or a complete perimeter of the aperture 954. The non-elastic structures 956 may be separate for each aperture 954 or they may be interconnected. FIG. 11A to 11C depicts still another embodiment of an elastic support 970 with flaps 972 comprises an elastic material such that a specific elastomeric member is not used. In this particular embodiment, the elastic support 970 comprise an open channel 974 that lacks discrete apertures and instead is generally open along the length of the channel 974 to the edges 922 and space 924 of the underlying incision or wound. As shown in FIGS. 11A to 11C, the elastic support 970 may be applied to an incision 976 closed with sutures 978 or other type of incision closure such as staples. The sutures 978 may any type of suture and may be used with any of a variety of suture techniques, including running sutures and interrupted sutures. In some variations, although the sutures 978 may generally maintain the approximation of the wound edges 980, separation forces acting at the sutures 978 may generate focal regions of tissue tension. Application of the elastic support 970 to the incision may be used to apply additional contiguous force along a substantial length of the incision 976, which may or may not reduce the focal tissue tension and possibly improve incision healing.

Figure 12:
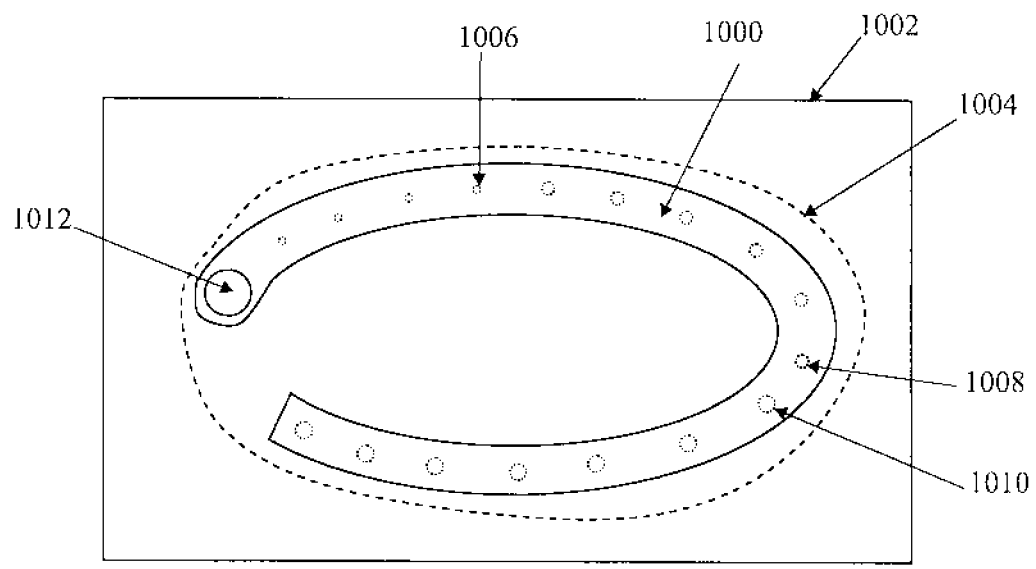
FIG. 12 is a schematic illustration of an elongate negative pressure therapy system arranged around a perimeter of a wound.

In other embodiments, the devices described herein may also be used to treat non-elongate incisions or wounds. FIGS. 12 to 15 depict various examples of using an elongate negative pressure therapy system to treat non-elongate wounds. In FIG. 12, for example, an elongate negative pressure therapy device 1000 and a sealant layer 1002 are positioned around the perimeter of wound 1004. As further illustrated in this example, the device 1000 may comprise apertures 1006, 1008 and 1010 of varying size. In some instances, smaller apertures 1004 may be used at distances closer to the suction source or interface 1012, while larger apertures 1008 may be used at relatively farther distances. In still other examples, the size of the apertures may be uniform, but either the number and/or the spacing of the apertures may vary along the longitudinal length of the device.

Figure 13:
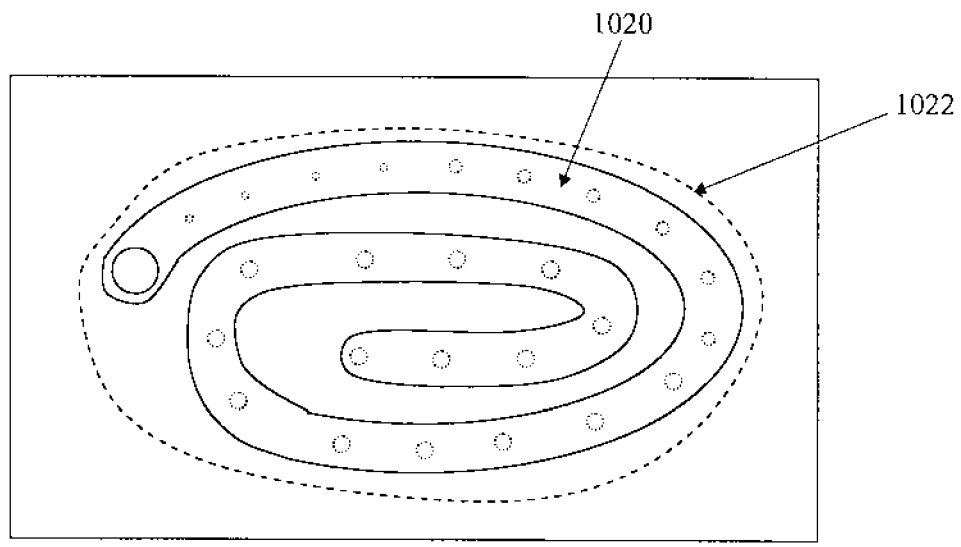
FIG. 13 is schematic illustration of an elongate negative pressure therapy system arranged in a spiral orientation about a wound.
Figure 14:
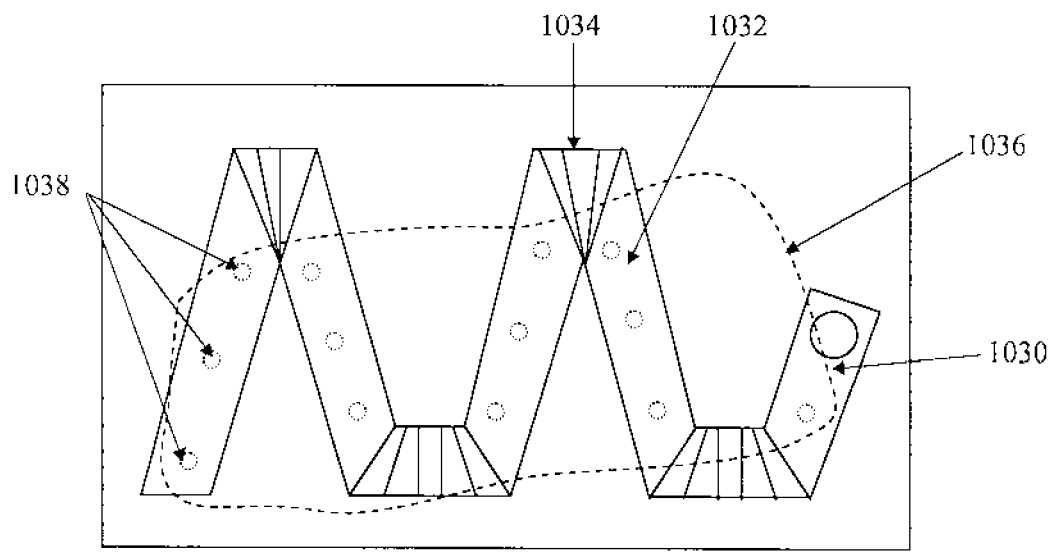
FIG. 14 is schematic illustration of an elongate negative pressure therapy system arranged in a zig-zag orientation about a wound.

FIG. 13 depicts another example of a negative pressure therapy device 1020 arranged in a spiral orientation with respect to a wound 1022. In some instances, the spiral orientation may augment the pressure or suction about the center of the wound 1022, compared to the device arranged depicted in FIG. 12. FIG. 14 is still another example of a device 1030 comprising alternating rigid sections 1032 and flexion sections 1034 arranged in a back-and-forth or zigzag orientation along a non-elongate wound 1036. As mentioned previously, in some examples, the rigid sections 1032 may also rotate with respect to the flexion section 1034 or other articulation of the device. As shown in FIG. 13, the device need not be fully located within the borders of the wound 1036, and although all of the device apertures 1038 are located within the wound borders, in other examples one or more apertures may be located outside the border of the wound.

Figure 15:
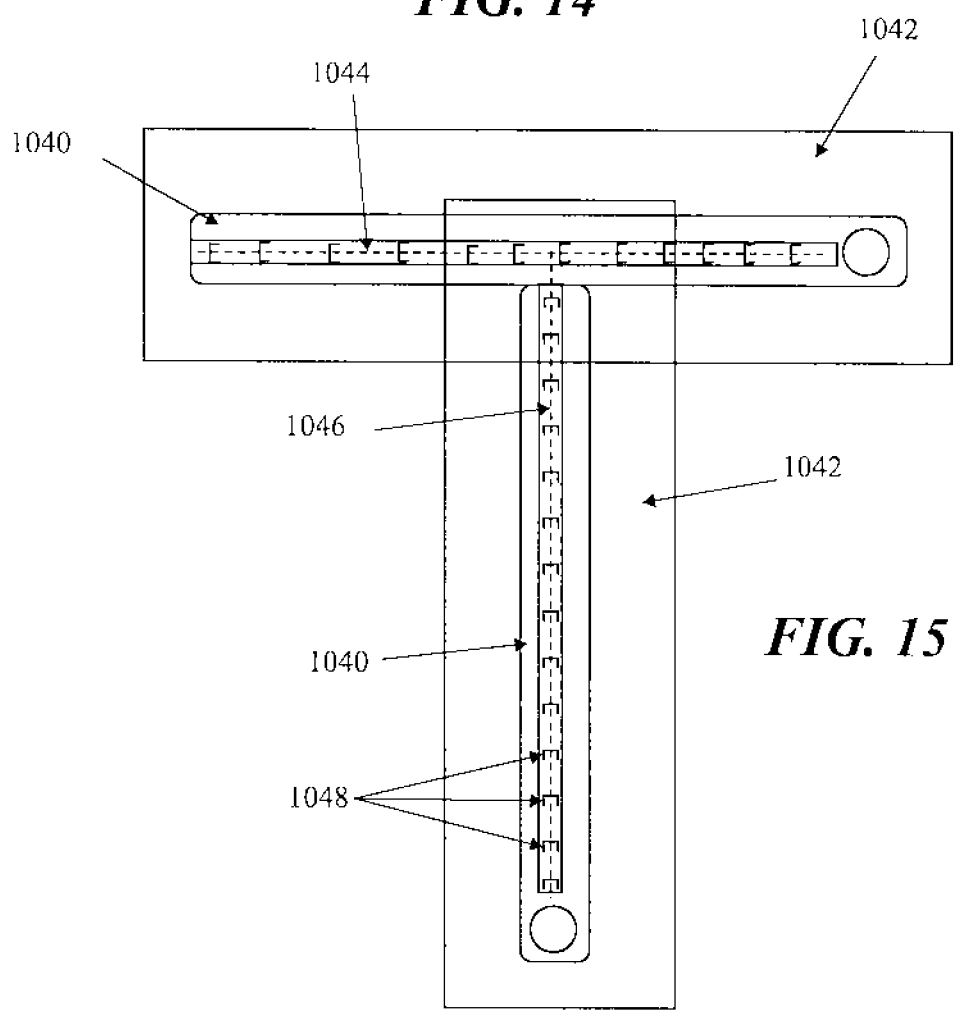
FIG. 15 is schematic illustration of an elongate negative pressure therapy system arranged in a T-orientation about a wound.

FIG. 15 depicts another example where multiple devices 1040 and sealant layers 1042 are used to close a non-linear surgical incision. In this particular embodiment, the surgical incision comprising a T-incision with a transverse incision 1044 and a midline incision 1046, and is treated using two open-channel devices 1040 applied to each incision 1044 and 1046, with overlapping sealant layers 1042. In other examples, more than two devices and two sealant layers may be used, e.g. one longer device may be used along the entire length of the midline incision 1046 and two smaller devices may be used along each remaining segment of the transverse incision 1044. In some instances, open channel devices 1040 may be used when surgical close is performed with staples 1048 or any other protruding closure component.

While a number of embodiments have been shown and described herein, one of skill in the art will understand that these embodiments are provided by way of example only. Numerous variations, changes, and substitutions may be made those skilled in the art without departing from the invention. It should be understood that various alternatives to the embodiments described herein may also be employed. It is intended that the following claims define the scope of the invention and that methods and structures within the scope of these claims and their equivalents be covered thereby. For all of the embodiments described herein, the steps of the methods need not be performed sequentially.

What is claimed:

1. A device to treat an area of skin trauma, the device comprising:
    (a) a first material layer configured to:
        seal to the area of skin trauma and,
        form a sealed space around at least a portion of the area of skin trauma;
    (b) a second material layer positioned beneath the first material layer to receive direct contact with the area of skin trauma; and
    (c) an elastic element configured to
        attach to the area of skin trauma while in a state of tension so that the elastic element extends across and over a longitudinal axis of the area of skin trauma, and
        compress the area of skin trauma when attached to the area of skin trauma.

2. The device of claim 1, further comprising a suction source configured to communicate fluid with the sealed space and reduce a level of pressure inside the sealed space.

3. The device of claim 1, wherein the second material layer comprises a plurality of openings, and wherein the plurality of openings are configured to communicate fluid between the second material layer and the area of skin trauma.

4. The device of claim 1, further comprising a one-way flow valve configured to facilitate an evacuation of the sealed space.

5. The device of claim 4, wherein the one-way flow valve is configured to facilitate emptying of the sealed space.

6. The device of claim 1, wherein the second material layer is configured to deliver one or more agents that improve a healing process.

7. The device of claim 1, wherein at least one of the second material layer or the first material layer includes at least one of silver, silver alloy, iodine, or chlorhexidine.

8. The device of claim 7, wherein the second material layer is a porous dressing interface.

9. The device of claim 1, wherein the second material layer is configured to conform to a length of the area of skin trauma.

10. The device of claim 1, wherein the first material layer is configured to conform to a length of the area of skin trauma.

11. The device of claim 1, wherein the first material layer is semi-rigid.

12. The device of claim 1, wherein the first material layer is configured to provide tensile support to the area of skin trauma to alleviate mechanical tension.

13. The device of claim 1, wherein the device further comprises one or more absorbent beads configured to absorb fluid at the area of skin trauma.

14. The device of claim 1, wherein the first material layer is further configured to deliver one or more antimicrobial agents to the area of skin trauma.

15. The device of claim 1, wherein the device is configured to deliver reduced pressure between about 0.001 to about 1 atmosphere at the area of skin trauma.

16. The device of claim 1, wherein the first material layer comprises a hydrocolloid material.

17. The device of claim 16, wherein the first material layer is configured to protect the area of skin trauma and prevent a trapping of fluid under the device.

18. The device of claim 1, wherein the first material layer further comprises a release liner coupled to a lower surface of the first material layer.

19. The device of claim 18, wherein the first material layer and release liner are in a rolled configuration and are configured to dispense and separate from each other as the first material layer seals to the area of skin trauma.

\* \* \* \* \*